US011618915B2

(12) United States Patent
Broder et al.

(10) Patent No.: US 11,618,915 B2
(45) Date of Patent: Apr. 4, 2023

(54) MULTI-WELL SAMPLE TESTING APPARATUS AND METHODS OF SAMPLE TESTING USING THE SAME

(71) Applicant: IDEXX Laboratories Inc., Westbrook, ME (US)

(72) Inventors: Daniel H. Broder, South Portland, ME (US); Lawrence G. Chapper, Andover, ME (US); Veronica L. Newport, Westbrook, ME (US); Julie E. Rollins, South Portland, ME (US); Brian M. Swalla, Scarborough, ME (US); Scott W. Wagner, York, ME (US); David L. White, Windham, ME (US)

(73) Assignee: IDEXX LABORATORIES INC., Westbrook, ME (US)

( * ) Notice: Subject to any disclaimer, the term of this patent is extended or adjusted under 35 U.S.C. 154(b) by 901 days.

(21) Appl. No.: 16/193,695

(22) Filed: Nov. 16, 2018

(65) Prior Publication Data

US 2019/0085371 A1 Mar. 21, 2019

Related U.S. Application Data

(63) Continuation of application No. 14/467,223, filed on Aug. 25, 2014, now abandoned.

(51) Int. Cl.
*C12M 1/32* (2006.01)
*C12M 1/04* (2006.01)
(Continued)

(52) U.S. Cl.
CPC ............ *C12Q 1/04* (2013.01); *B01L 3/50853* (2013.01); *C12M 23/12* (2013.01); *C12M 23/24* (2013.01);
(Continued)

(58) Field of Classification Search
None
See application file for complete search history.

(56) References Cited

U.S. PATENT DOCUMENTS 3,660,033 A 5/1972 Schwartz
3,787,290 A 1/1974 Kaye
(Continued)

FOREIGN PATENT DOCUMENTS

CN 101827931 A 9/2010
EP 2446966 A1 5/2012
(Continued)

OTHER PUBLICATIONS

Quanti-Tray® Quanti-Tray®/2000 product brochure, IDEXX, (2002), 2 pages. (Year: 2002).*
(Continued)

*Primary Examiner* — William H. Beisner
(74) *Attorney, Agent, or Firm* — Carter, DeLuca & Farrell LLP

(57) ABSTRACT

A sample testing apparatus includes a sample tray defining a planar surface and a plurality of wells recessed relative to the planar surface, and a lid member configured to be sealed about the planar surface of the sample tray. The lid member includes an adhesive layer configured to be sealed to the planar surface of the sample tray, a breathable film layer disposed about the adhesive layer, and a backing layer disposed about the breathable film layer. Methods of using the sample testing apparatus for testing a sample and kits to facilitate such testing are also provided.

20 Claims, 13 Drawing Sheets

(51) Int. Cl.
  *C12Q 1/04* (2006.01)
  *B01L 3/00* (2006.01)
(52) U.S. Cl.
  CPC .................. *B01L 2200/0684* (2013.01); *B01L 2200/0689* (2013.01); *B01L 2200/141* (2013.01); *B01L 2200/16* (2013.01); *B01L 2300/048* (2013.01); *B01L 2300/0654* (2013.01); *B01L 2300/0829* (2013.01); *B01L 2300/0851* (2013.01); *B01L 2300/0887* (2013.01); *B01L 2300/123* (2013.01); *B01L 2300/126* (2013.01)

(56) References Cited

U.S. PATENT DOCUMENTS

| | | | |
|---|---|---|---|
| 4,129,483 | A | 12/1978 | Bochner |
| 4,245,043 | A | 1/1981 | Lund |
| 4,245,052 | A * | 1/1981 | Lund ................... B01L 3/5085 356/246 |
| 5,244,677 | A | 9/1993 | Kreckel et al. |
| 5,518,892 | A | 5/1996 | Naqui et al. |
| 5,620,895 | A | 4/1997 | Naqui et al. |
| 5,665,247 | A | 9/1997 | Valus et al. |
| 5,721,136 | A | 2/1998 | Finney et al. |
| 5,753,456 | A | 5/1998 | Naqui et al. |
| 5,800,778 | A | 9/1998 | Chen et al. |
| 5,853,586 | A | 12/1998 | Valus et al. |
| 5,858,770 | A | 1/1999 | Perlman |
| 5,891,077 | A | 4/1999 | Gilman et al. |
| 6,037,168 | A | 3/2000 | Brown |
| 6,245,295 | B1 | 6/2001 | Chen et al. |
| 6,632,652 | B1 | 10/2003 | Austin et al. |
| 6,682,702 | B2 | 1/2004 | Barth et al. |
| 7,318,590 | B2 | 1/2008 | Razavi |
| 7,781,185 | B2 | 8/2010 | Goldman et al. |
| 8,486,692 | B2 | 7/2013 | Simon |
| 2001/0024805 | A1 * | 9/2001 | Williams ............... C12M 41/36 435/29 |
| 2002/0173033 | A1 | 11/2002 | Hammerick et al. |
| 2008/0206857 | A1 | 8/2008 | Kenney et al. |
| 2009/0053773 | A1 | 2/2009 | Sato et al. |
| 2011/0286897 | A1 * | 11/2011 | Uschkureit ......... B29C 45/0081 422/553 |
| 2014/0255912 | A1 | 9/2014 | Myles |

FOREIGN PATENT DOCUMENTS

| | | |
|---|---|---|
| JP | H0718600 A | 1/1995 |
| JP | H09509609 A | 9/1997 |
| JP | 2007529001 A | 10/2007 |
| JP | 2008-532539 | 8/2008 |
| JP | 2009011260 A | 1/2009 |
| JP | 2012060903 A | 3/2012 |
| JP | 2012518411 A | 8/2012 |
| JP | 2013040290 A | 2/2013 |
| WO | 01/74991 A1 | 10/2001 |
| WO | 2010150415 A1 | 12/2010 |

OTHER PUBLICATIONS

Australian Examination Report for Application No. 2015306974 dated May 29, 2020.
First Office Action issued in corresponding Chinese Application No. 201580058032.X dated Nov. 29, 2018, with English translation, 17 pages.
Japanese Office Action issued in corresponding Japanese Application No. 2017-511197 dated Jul. 2, 2019, 10 pages.
Chinese Office Action issued in corresponding Chinese Application No. 201580058032.X dated Jul. 10, 2019, 26 pages.
Invitation to Pay Additional Fees with Partial Search Report issued in corresponding application No. PCT/US2015/045907 dated Nov. 6, 2015.
Notification of Transmittal of the International Search Report and the Written Opinion of the International Searching Authority, or the Declaration issued in corresponding application No. PCT/US2015/045907 dated Jan. 18, 2016.
Japanese Office Action issued in corresponding Japanese Application No. 2019-181470 dated Oct. 10, 2020, 8 pages.
Extended European Search Report issued in corresponding European Application No. EP 21173758.0, dated Jul. 30, 2021, pp. 1-6.
Mexican Office Action issued in corresponding MX Application No. MX/a/2017/002471 dated Apr. 20, 2022, pp. 1-13, together with English-language translation.
New Zealand Examination Report issued in corresponding NZ Application No. 730132 dated Jan. 20, 2022, pp. 1-5.
Chinese Office Action issued in corresponding Chinese Application No. CN201910897649.0 dated Jan. 12, 2022, pp. 1-6.
Mexican Office Action issued in corresponding MX Application No. MX/a/2017/002471, dated Oct. 13, 2022, pp. 1-17, together with English-language translation.
Canadian Office Action issued in corresponding CA Application No. 2,959,327 dated Jul. 25, 2022, pp. 1-3.
Korean Office Action issued in corresponding KR Application No. 10-2017-7007754, dated Oct. 25, 2022, pp. 1-15, together with English-language translation.
Chinese Rejection Decision issued in corresponding CN Application No. 201910897649.0 dated Aug. 3, 2022, pp. 1-14.
New Zealand Examination Report issued in corresponding NZ Application No. 730132 dated Jul. 13, 2022, pp. 1-3.

* cited by examiner

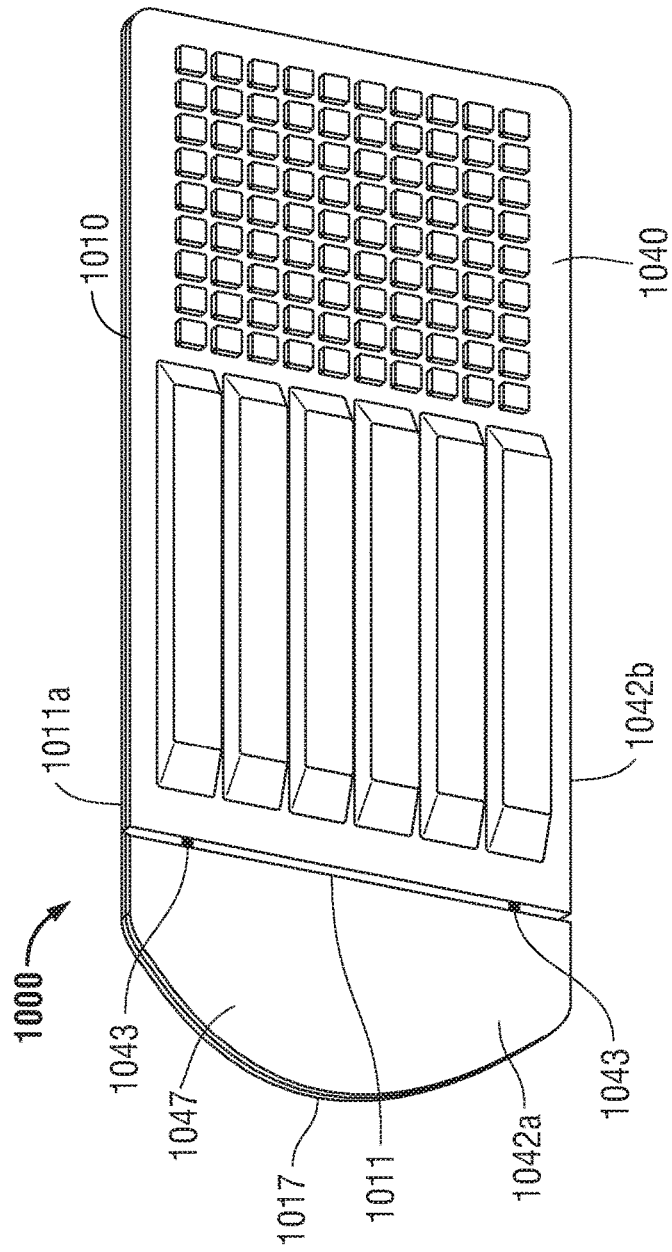
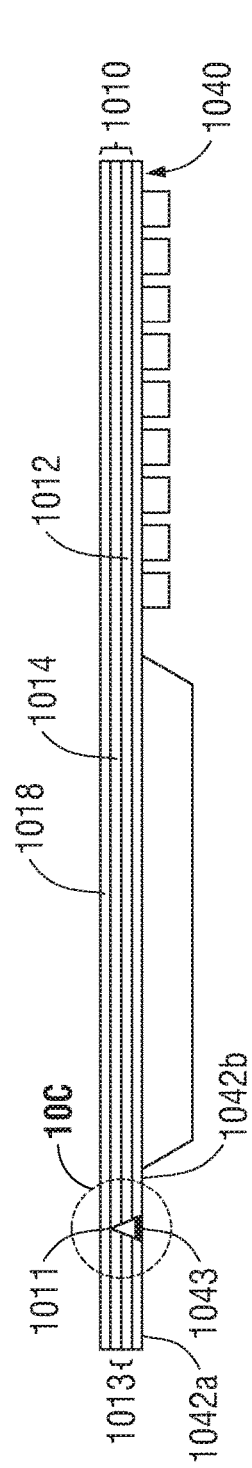
FIG. 10A
FIG. 10B

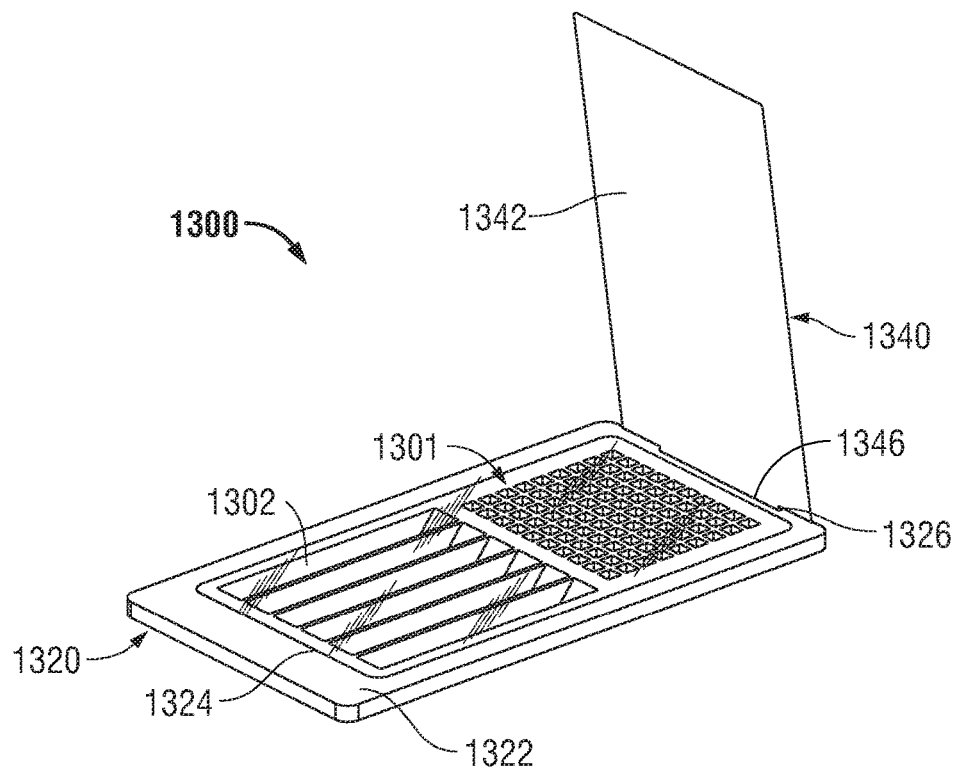
FIG. 13A
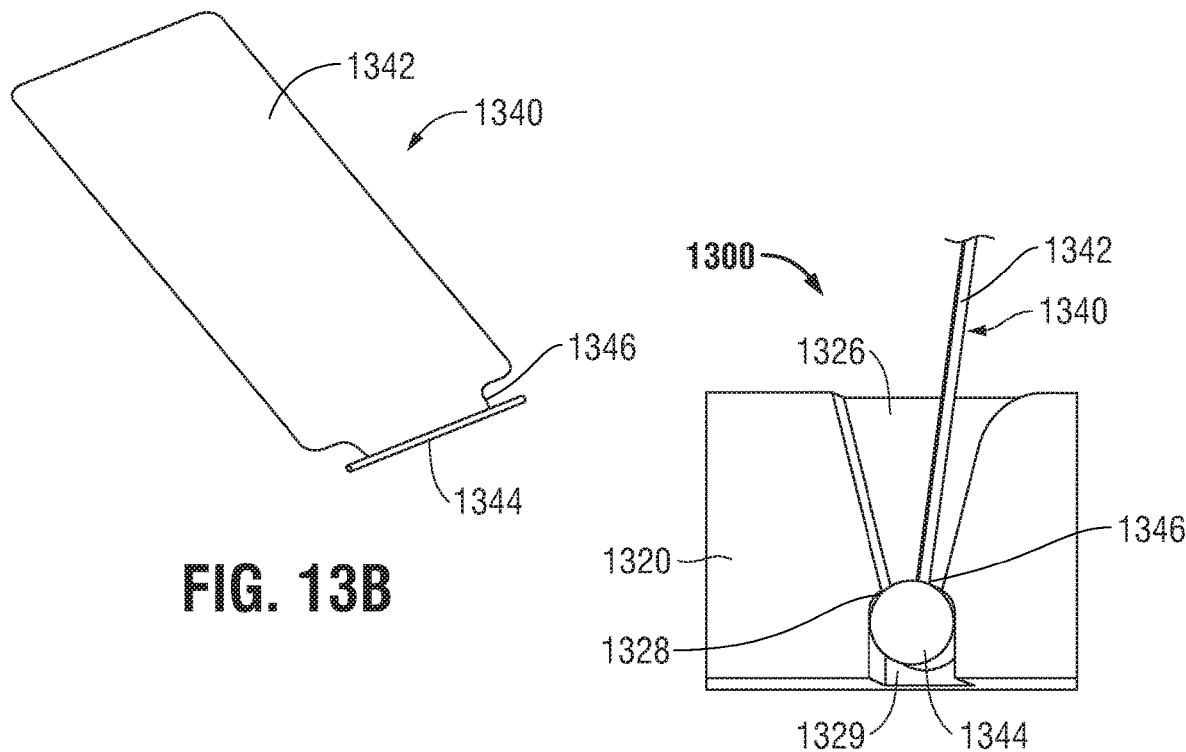
FIG. 13B
FIG. 13C

MULTI-WELL SAMPLE TESTING APPARATUS AND METHODS OF SAMPLE TESTING USING THE SAME

CROSS-REFERENCE TO RELATED APPLICATIONS

This application is a continuation application of U.S. patent application Ser. No. 14/467,223, filed on Aug. 25, 2014, the entire contents of which are hereby incorporated herein by reference.

BACKGROUND

Technical Field

The present disclosure relates to sample testing and, more particularly, to multi-well sample testing apparatus and methods of sample testing using the same.

Background of Related Art

Many industries rely on the detection and quantification of the concentration and/or level of biological material in a liquid sample. For example, the determination of bacterial concentration in water is an essential part of water quality testing. EPA regulations require that no Coliform or *Escherichia coli* be present in potable water. The "presence/absence" format for testing a medium is very useful in making this determination.

Other tests require quantification, not just detection, of bacterial concentration in a liquid sample. Examples of such include the testing of waste water, incoming water in water purification systems, surface water, and food testing. Traditional methods of quantification of biological material include membrane filtration and the most probable number (MPN) method.

With respect to membrane filtration, the required volume of sample is filtered through a membrane of a very small pore size to non-specifically trap bacteria. The membrane is then placed on a medium which supports the growth of the target bacteria. The medium is incubated at a specific temperature for a specific time and any resulting colonies are counted.

The MPN method involves dispensing a volume of liquid sample and a testing medium into a plurality of tubes. After incubation at a specific temperature for a specific time, the number of positive tubes is counted. The MPN for a given volume can then be calculated based upon the number of positive tubes, the sample volume in the negative tubes, and the total sample volume in all of the tubes. Exemplary microbiological quantification devices and methods using the MPN method are detailed in U.S. Pat. Nos. 5,518,892; 5,620,895; and 5,753,456 to Naqui et al., the entire contents of each of which is incorporated herein by reference.

SUMMARY

To the extent consistent, any of the aspects detailed herein may be used in conjunction with any of the other aspects detailed herein.

In accordance with the present disclosure, a sample testing apparatus is provided including a sample tray and a lid member. The sample tray defines a planar surface and includes a plurality of wells recessed relative to the planar surface. The lid member includes an adhesive layer configured to be sealed to the planar surface of the sample tray, a breathable film layer disposed about the adhesive layer, and a backing layer disposed about the breathable film layer.

In aspects, the sample tray is formed from a permeable, transparent, non-toxic material. For example, the sample tray may be formed from a blend of a styrene butadiene copolymer and general purpose polystyrene.

For purposes of this application the terms "breathable" and "permeable" mean the ability to transmit gases and vapors through the barriers disclosed herein.

In aspects, the adhesive layer is formed from a material that is permeable, transparent, and capable of being heat sealed to the planar surface of the sample tray. For example, the adhesive layer may be formed from ethylene vinyl acetate or modified ethylene vinyl acetate.

In aspects, the adhesive layer includes a plurality of perforations. Each perforation corresponds to and is positioned for alignment with one of the wells defined within the sample tray such that the adhesive layer does not extend over any portion of the wells.

In aspects, the breathable film layer is formed from a material that is permeable and preferably transparent. For example, the breathable film layer may be formed from a thermoplastic copolyester based elastomer.

In aspects, the backing layer is a paper backing layer including a paper that is permeable, insulating, and capable of adhesive-less bonding to the breathable film layer. For example, the backing layer may be formed from a kraft paper, a clay-coated paper, or an offset paper.

In aspects, the backing layer is configured as a release liner that is removable, e.g., peelable, from the breathable film layer.

In aspects, the release liner includes a paper layer and a silicone layer. The release liner may further include a polyester layer.

In aspects, a perforation extends through the sample tray and partially through the lid member to facilitate removal of the release liner. Further, at least one connector may be provided to interconnect the portions of the sample tray on either side of the perforation. The at least one connector may be breakable to permit removal of the release liner, e.g., upon initiation of peeling-off of the release liner.

In aspects, the plurality of wells include a first set of wells and a second set of wells. In some aspects, a third set of wells is provided. Each set of wells defines a different configuration, e.g., shape, volume, etc.

In aspects, the lid member is initially sealed to the sample tray about a first peripheral side, a second peripheral side, and a bottom end of the sample tray to define a pouch. An open top end of the sample tray is configured to permit introduction of a liquid sample into the pouch. The lid member may further be configured to be sealed about the sample tray by heat sealing the adhesive layer to the planar surface, thereby sealing each of the wells with a portion of the liquid sample therein.

In aspects, the lid member is sealed to the sample tray entirely about an outer perimeter of the planar surface of the sample tray to define a pouch therebetween. In such aspects, the sample tray defines a slit extending therethrough that is configured to permit introduction of a liquid sample into the pouch.

In aspects, the sample tray includes at least one reinforcement member configured to provide structural support to the sample tray.

In aspects, the sample tray defines at least one bridge fluidly connecting adjacent wells to facilitate the capture of an air bubble within at least one of the adjacent wells upon sealing of the lid member with the sample tray.

Another sample testing apparatus provided in accordance with the present disclosure includes a sample tray and a lid member. The sample tray defines a planar surface and includes a plurality of wells recessed relative to the planar surface. The lid member is configured to be sealed to the planar surface of the sample tray to seal each of the plurality of wells. An insert positioned between the sample tray and the lid member is configured to capture an air bubble within at least one of the wells.

In aspects, the insert includes a dissolvable film configured to dissolve upon contact with a liquid sample. The dissolvable film defines at least one well. The at least one well of the dissolvable film is configured for positioning within a corresponding well of the sample tray. More specifically, the at least one well of the dissolvable film may define a reduced depth relative to the corresponding well of the sample tray to define an air pocket therebetween. Further, the dissolvable film may be formed from polyvinyl alcohol.

In aspects, the insert includes a plate defining a plurality of cut-outs. Each cut-out is configured for positioning about a corresponding well and defines a reduced opening in at least one dimension as compared to an opening of the corresponding well.

Another sample testing apparatus provided in accordance with the present disclosure includes a sample tray and a lid member. The sample tray defines a planar surface and includes a plurality of wells recessed relative to the planar surface. The lid member is configured to be sealed to the planar surface of the sample tray to seal each of the plurality of wells. At least one bridge is provided to fluidly connect adjacent wells. The at least one bridge is configured to facilitate the capture of an air bubble within at least one of the adjacent wells upon sealing of the lid member with the sample tray.

Another sample testing apparatus provided in accordance with the present disclosure includes a sample tray and a lid member. The sample tray defines a planar surface and includes a plurality of wells recessed relative to the planar surface. The lid member is configured to be sealed to the planar surface of the sample tray to seal each of the plurality of wells. At least one dissolvable capsule is provided. Each dissolvable capsule is disposed within one of the wells of the sample tray and is configured to dissolve to provide an air bubble within the well.

A method of testing a sample provided in accordance with the present disclosure includes providing a sample testing apparatus including a sample tray and a lid member. The sample tray defines a plurality of wells including a first set of wells having a first configuration and a second set of wells having a second configuration. Additional sets, e.g., a third set of wells having a third configuration, are also contemplated. The lid member is sealed to the sample tray about at least a first peripheral side, a second peripheral side, and a bottom end of the sample tray and defines a pouch therebetween. The method further includes introducing a predetermined volume of a liquid sample into the pouch of the sample testing apparatus and sealing the lid member to the sample tray to seal each of the plurality of wells such that each of the wells of the first set of wells is filled to capacity with a first portion of the liquid sample and such that a remainder of the liquid sample is evenly distributed into the wells of the second set of wells. The volume of liquid sample in each of the wells of the second set of wells may be less than a volume capacity of each of the wells in the second set of wells.

In aspects, sealing the lid member to the sample tray is performed via heat sealing. The sample tray may be positioned within a receptacle prior to heat sealing. Further, the sample tray may be enclosed within the receptacle using a cover flap prior to heat sealing.

In aspects, the method further includes incubating the sealed sample testing apparatus. Incubating the sealed sample testing apparatus may be performed with the lid member facing downward, i.e., inverted.

In aspects, the method further includes peeling off a backing layer of the lid member prior to incubating the sealed sample testing apparatus.

In aspects, peeling off the backing layer includes grasping the backing layer at a central apex thereof and peeling off the backing layer such that the peeling off is initiated adjacent a center of the sample tray. Alternatively, peeling may be initiated from either top corner of the sample tray.

In aspects, the method further includes counting a number of positive wells and determining a result based upon the number of positive wells.

In aspects, the lid member is sealed to a bottom of the sample tray and unsealed at a top of the sample tray. In such aspects, introducing the predetermined volume of the liquid sample into the pouch includes introducing the predetermined volume through the unsealed top.

In aspects, the lid member is sealed about a perimeter edge of the sample tray. In such aspects, introducing the predetermined volume of the liquid sample into the pouch includes introducing the predetermined volume through a slit defined within the sample tray.

A kit provided in accordance with the present disclosure includes a sample testing apparatus and a receptacle. The sample testing apparatus generally includes a sample tray defining a plurality of wells, and a lid member disposed to cover the plurality of wells. The sample testing apparatus may further be configured to include any of the aspects detailed above. The receptacle is configured to receive the sample testing apparatus and includes a base portion and, in some aspects, a cover flap. The base portion defines a cavity for receipt of the sample testing apparatus therein. The cover flap is releasably engagable with the base portion. When engaged to the base portion, the cover flap is pivotable relative to the base portion between an open position permitting insertion and withdrawal of the sample testing apparatus from the cavity, and a closed position wherein the cover flap encloses the sample testing apparatus within the receptacle.

In aspects, the base portion includes a cut-out defined adjacent an outer peripheral edge thereof. The cut-out is configured to facilitate insertion or withdrawal of the sample testing apparatus to/from the cavity.

In aspects, the cavity includes a plurality of discrete chambers. Each chamber is configured to receive one of the plurality of wells of the sample testing apparatus upon insertion of the sample testing apparatus into the cavity.

In aspects, the base portion of the receptacle defines an engagement slot and the cover flap includes an engagement pin coupled thereto. The engagement pin is configured for snap-fit engagement within the engagement slot to releasably couple the cover flap to the base portion. More specifically, the engagement slot may include a shoulder configured to inhibit withdrawal of the engagement pin from the engagement slot, or the engagement slot may include a neck portion and an enlarged portion wherein the neck portion inhibits withdrawal of the engagement pin from the enlarged portion.

In aspects, the base portion of the receptacle includes at least one finger spaced-apart from the base portion to define an engagement area therebetween. In such aspects, the cover flap includes an engagement pin coupled thereto that is configured for releasable positioning within the engagement area to releasably couple the cover flap to the base portion.

In aspects, the base portion of the receptacle defines at least one first lumen and the cover flap defines at least one second lumen. The first and second lumens are configured to align with one another to permit insertion of an engagement pin therethrough to releasably couple the cover flap to the base portion.

BRIEF DESCRIPTION OF THE DRAWINGS

Various aspects of the present disclosure are described herein with reference to the drawings wherein like reference numerals identify similar or identical elements:

FIG. 10A is a bottom, perspective view of another multi-well sample testing apparatus provided in accordance with the present disclosure;

FIG. 10B is a side view of the apparatus of FIG. 10A;

FIG. 13A is a perspective view of a sealing insert provided in accordance with the present disclosure, shown including a multi-well sample testing apparatus positioned therein;

FIG. 13B is a perspective view of a cover of the sealing insert of FIG. 13A;

FIG. 13C is a transverse, cross-sectional view of the engagement between the cover and a base of the sealing insert of FIG. 13A;

DETAILED DESCRIPTION

Provided in accordance with the present disclosure and detailed below are apparatus and methods that facilitate the detection and/or quantification of biological material, e.g., bacteria, fungi or other living organisms, aggregates of proteins such as enzymes, co-factors using reaction mixtures, etc., within a liquid sample. A testing medium, e.g., chemical and/or microbiological reactants, suitable for enabling detection of the specific biological material to be quantified is introduced into the liquid sample prior to testing. As can be appreciated, the testing medium utilized will depend on the biological material to be detected. More specifically, a testing medium is selected that enables detection of the presence of the biological material sought to be quantified, preferably does not detect the presence of other biological material likely to be present in the liquid sample, and provides a sensible change, e.g., color change, fluorescence, etc., if the biological material sought to be detected is present in the liquid sample. Exemplary tests capable of being performed using the apparatus and methods of the present disclosure include the detection of: Coliforms and *E. coli, Legionella*, Enterococci, and *Pseudomonas aeruginosa* (e.g., using the Pseudalert® test kit, manufactured by IDEXX Laboratories, Inc. of Westbrook, Me., USA). Other suitable tests are also contemplated.

Figure 1A:
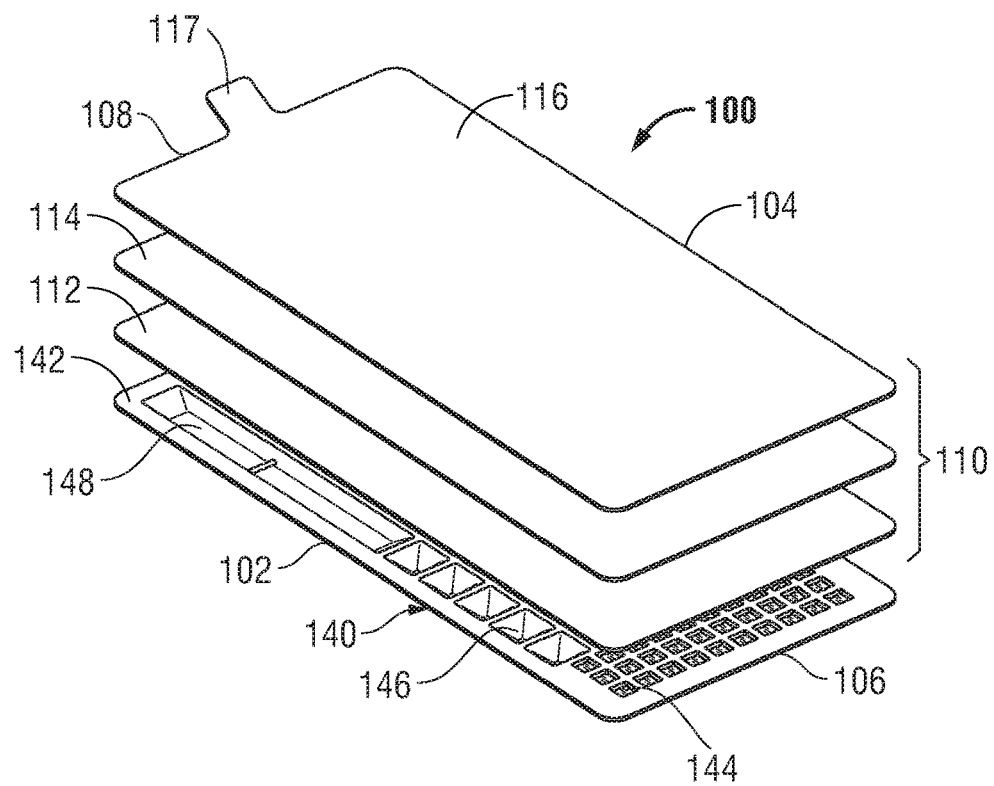
FIG. 1A is an exploded, perspective view of a multi-well sample testing apparatus provided in accordance with the present disclosure.
Figure 1B:
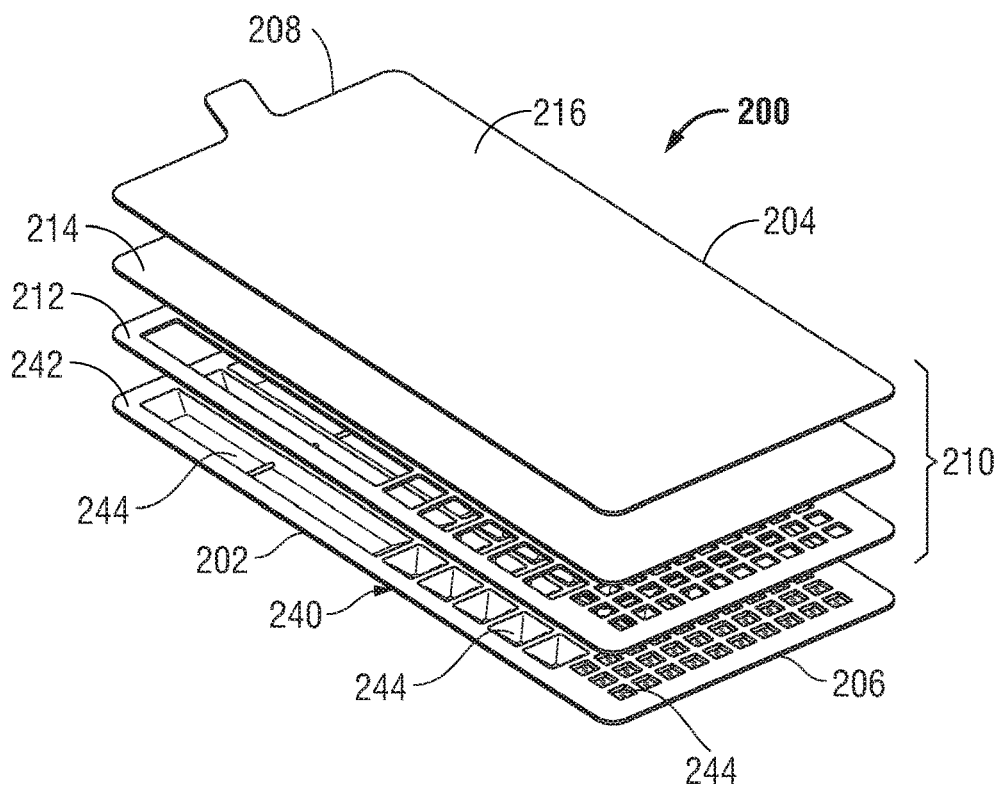
FIG. 1B is an exploded, perspective view of another multi-well sample testing apparatus provided in accordance with the present disclosure.

Turning to FIGS. 1A-1B, multi-well sample testing apparatus 100, 200 provided in accordance with the present disclosure are shown each generally including a lid member 110, 210 and a sample tray 140, 240. The lid members 110, 210 and sample trays 140, 240 of the respective apparatus 100, 200 define generally rectangular configurations of similar dimension and are sealingly engaged to one another along three edges of the apparatus 100, 200, e.g., side edges 102, 104 and 202, 204 and bottom edges 106, 206, respectively, so as to define a pouch-like configuration. Open top edges 108, 208 of the apparatus 100, 200 permit the introduction of the liquid sample to be tested (including the testing medium) into the interior of the pouch, as will be detailed below.

With reference to FIG. 1A, the lid member 110 of the apparatus 100 is formed from three layers of material: an adhesive layer 112, a breathable film layer 114, and a backing layer 116. The backing layer 116 is optional and preferably paper. The adhesive layer 112 is configured to interface directly with the sample tray 140 to adhere the lid member 110 to the sample tray 140 upon heat sealing, as will be detailed below. The material forming the adhesive layer 112 is selected based upon its ability to seal to the sample tray 140 via heat sealing, provide some degree of permeability without allowing for excess liquid sample loss during incubation, and for its transparency. In embodiments, the adhesive layer 112 is formed from a relatively thin sheet of ethylene vinyl acetate or modified ethylene vinyl acetate.

The breathable film layer 114 of the lid member 110 is disposed between the adhesive layer 112 and the paper backing layer 116. The material forming the breathable film layer 114 is selected based upon its permeability, ability to withstand the relatively high temperatures of heat sealing, ability to withstand and not discolor during sterilization, transparency, and optimization with testing media, e.g., indicator reagents. In embodiments, the breathable film layer 114 is formed from a thermoplastic copolyester based elastomer. In other embodiments, the breathable film layer 114 may be formed from ethylene vinyl acetate or modified ethylene vinyl acetate, a thermoplastic copolymer, a thermoplastic polyurethane elastomer or aromatic polyether, a styrene butadiene copolymer, or fluorinated ethylene propylene.

The paper backing layer 116 of the lid member 110 is disposed on the breathable film layer 114. The material forming the paper backing layer 116 is selected based upon its permeability, ability to bond with the breathable film layer 114 without the need for an adhesive therebetween, ability to withstand the relatively high temperatures of heat sealing, printability, and insulating properties (i.e., the ability to allow the proper amount of heat transfer to the adhesive layer 112 during heat sealing). In embodiments, the paper backing layer 116 is formed from a kraft paper, or may alternatively be formed from an offset paper (preferably of 50 lb. weight, although other weights are also contemplated). Further, the paper backing layer 116 may be colored white to provide a suitable background to facilitate detection of a color change of the testing medium. Alternatively, the paper back layer 116 may be removable, e.g., peelable, after heat sealing of the lid member 110 to the sample tray 140 to expose the transparent breathable film layer 114. In such configurations, rather than providing a white background, apparatus 100 may be positioned adjacent a different color background or a light box to facilitate detection of a change in the testing medium. Providing a removable paper back layer 116 also increases the permeability of the lid member 110 during incubation by exposing the breathable film layer 114 and inhibits liquid sample loss during incubation due to the paper back layer 116 acting as a desiccant. The paper backing layer 116 may further include a tab 117 extending therefrom adjacent the open top edge 108 of the apparatus 100 to facilitate opening and/or handling of apparatus 100. In some embodiments, paper backing layer 116 is omitted.

With respect to manufacturing the lid member 110, the breathable film layer 114 is extruded and cast directly onto the paper backing layer 116, and the adhesive layer 112 is extruded and cast directly onto the breathable film layer 114. Alternatively, the adhesive layer 112 and the breathable film layer 114 may be cast onto the paper backing layer 116 during co-extrusion of the adhesive and breathable film layers 112, 114, respectively. The layers 112, 114, 116 may also be formed as separate films and laminated together.

Referring to FIG. 1B, the apparatus 200 is similar to the apparatus 100 (FIG. 1A) except for the configuration of the lid member 210. The apparatus 200 may further include any or all of the features of the apparatus 100 (FIG. 1A). For purposes of brevity, only the differences between the apparatus 200 and the apparatus 100 (FIG. 1A) are detailed below.

The lid member 210 of the apparatus 200 is formed from at least three layers of material: an adhesive layer 212, a breathable film layer 214, and a paper backing layer 216. The breathable film layer 214 and the paper backing layer 216 are similar to those detailed above with respect to the lid member 110 (FIG. 1A). The adhesive layer 212 differs from the adhesive layer 112 of the lid member 110 (FIG. 1A) in that the adhesive layer 212 is perforated, e.g., via die cutting, laser cutting, or other suitable manufacturing process, to remove the portions disposed over the wells 244 of the sample tray 240. As a result, during sealing, the adhesive layer 212 is sealed to the sample tray 240 over the entire surface 242 thereof, between and about each of the wells 244 defined within the sample tray 240, but does not extend across any of the wells 244 defined within the sample tray 240. This configuration provides increased permeability without compromising sealing integrity.

Figure 2:
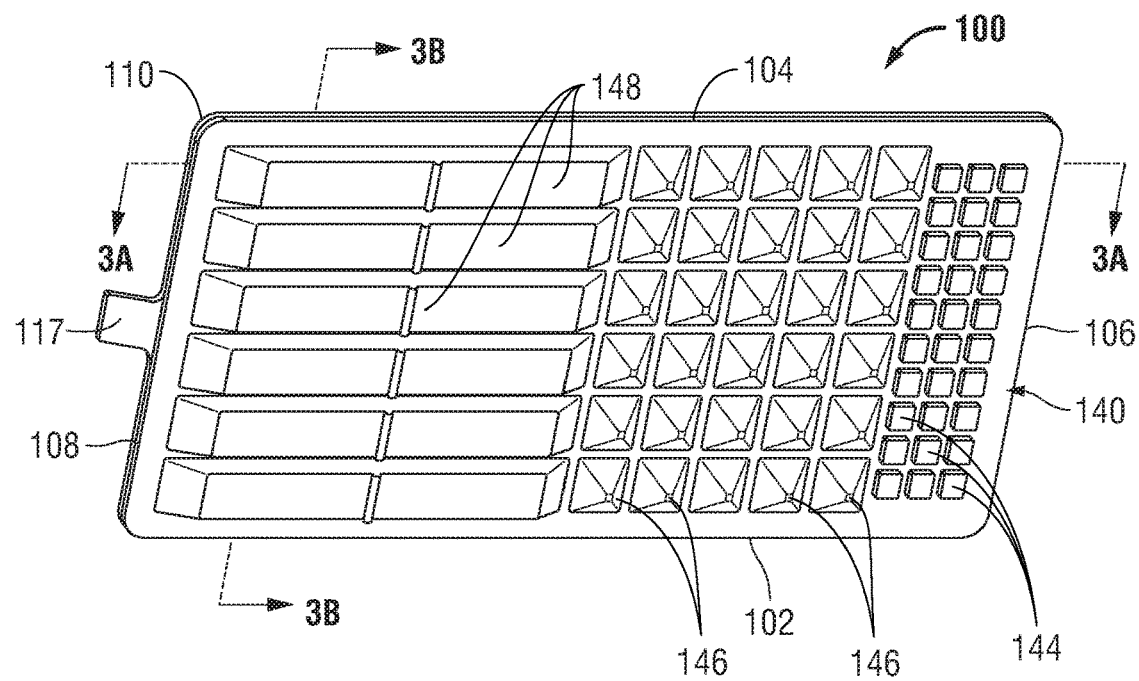
FIG. 2 is a bottom, perspective view of the apparatus of FIG. 1A.
Figure 3A:
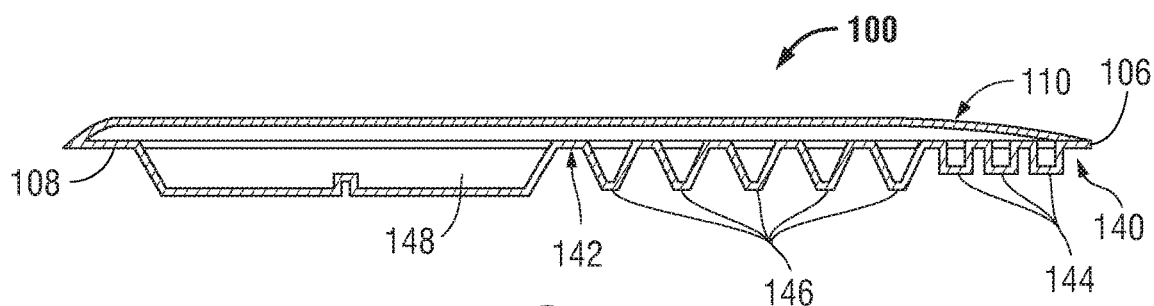
FIG. 3A is a cross-sectional view of the apparatus of FIG. 1A taken along section line "3A-3A" of FIG. 2.
Figure 3B:
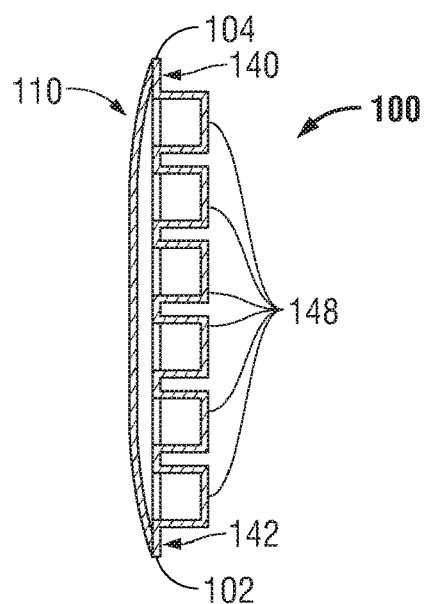
FIG. 3B is a cross-sectional view of the apparatus of FIG. 1A taken along section line "3B-3B" of FIG. 2.

Referring again to FIG. 1A, and with additional reference to FIGS. 2-3B, the sample tray 140 of the apparatus 100 defines a generally planar upper surface 142 and includes a plurality of sets of wells 144, 146, 148 of varying configuration recessed relative to the generally planar upper surface 142. More specifically, the sample tray 140 includes a plurality of small wells 144 positioned towards the sealed bottom edge 106 of the apparatus 100, a plurality of medium wells 146 positioned intermediate the sets of wells 144, 148, and a plurality of elongated large wells 148 positioned towards the open top edge 108 of the apparatus 100. The different configurations of the wells 144, 146, 148 eliminate the need to dilute the liquid sample and increase the range of quantification. Each of the sets of wells 144, 146, 148 will be described in greater detail, in turn, below. However, other configurations of wells of similar and/or varying configuration are also contemplated such as, for example, those disclosed in the '892, '895, and '456 Patents to Naqui et al., previously incorporated herein by reference.

The material forming the sample tray 140 is selected based upon its permeability, non-toxicity to the biological material being detected, ability to withstand and not discolor during sterilization, transparency, reduced or absent fluorescence, and its ability to be sealed to the adhesive layer 112 via heat sealing. In embodiments, the sample tray is formed from a blend of a styrene butadiene copolymer and general purpose polystyrene. This blend has been found to achieve the above-noted criteria. In particular, this blend has been found to be particularly suited for sealing to ethylene vinyl acetate or modified ethylene vinyl acetate, the material used to form the adhesive layer 112. Further, it has been found that this blend is advantageous in that it is non-toxic with respect to many biological materials to be detected, e.g., *Legionella* bacteria, while polyvinyl chloride has been found to be toxic to and kill certain biological materials, e.g., *Legionella* bacteria.

Referring to FIGS. 2-3B, the plurality of small wells 144 are arranged in a three by ten matrix positioned towards the sealed bottom edge 106 of apparatus 100. Each small well 144 is generally rectangular in configuration, although the side walls of each small well 144 angle slightly inwardly towards one another in the direction approaching the base of the small well 144. The relatively shallow configuration of the small wells 144 maximizes the ratio of lid member surface area above the well 144 to liquid sample volume retained within the well 144. It has been found that maximizing this ratio within sample wells helps optimize bacteria growth and maximize permeability. Preferably, this ratio is equal to or greater than about 0.33 cm$^2$/mL for all wells. In embodiments, each small well 144 defines a volume of 0.20 mL, is configured to receive about 0.20 mL of liquid sample (100% capacity), and defines a lid member surface area (in cm$^2$) to sample volume (in mL) ratio of about 0.67.

The plurality of medium wells 146 are arranged in a five by six matrix positioned between the small wells 144 and the large elongated wells 148. Each medium well 146 defines an inverted pyramid configuration with a rounded or flattened base. This configuration provides each of the medium wells 146 with an increased depth without requiring an increase in volume. This increased depth provides a longer "view path" through the liquid sample in the well 146. The longer "view path" provides better color differentiation, thus facilitating detection of whether there is a color change of the liquid sample (due to the testing medium) within the well 146. The inverted pyramid configuration of the medium wells 146 also maximizes the ratio of lid member surface area above the well 146 to liquid sample volume retained within the well 146. In embodiments, each medium well 146 defines a volume of about 1.01 mL, is configured to receive about 1.01 mL of liquid sample (100% capacity), and defines a lid member surface area (in cm$^2$) to sample volume (in mL) ratio of about 0.48.

The plurality of elongated large wells 148, e.g., six elongated large wells 148, are arranged to extend longitudinally in side-by-side relation and are positioned towards the open top edge 108 of apparatus 100. With the small and medium wells 144, 146, respectively, filled with the liquid sample to 100% capacity, the large elongated wells 148 receive the remainder of the liquid sample. The elongated configuration of the large wells 148 and the relatively shallow depth of the large wells 148 enables the large wells 148 to retain a relatively large volume of liquid sample without compromising the ratio of lid member surface area above the wells 148 to liquid sample volume retained within the wells 148. In embodiments, each large elongated well 148 defines a volume of about 18.86 mL, is configured to receive about 10.95 mL of liquid sample (about 58% capacity, with the remaining volume occupied by air), and defines a lid member surface area (in cm$^2$) to sample volume (in mL) in each well 148 ratio of about 0.35. The about 58% capacity of the large elongated wells 148, as will be detailed below, is a result of the liquid sample first being utilized to fill the small and medium wells 144, 146, respectively, to capacity using a 100 mL sample, with the remaining liquid sample then being equally distributed into the large wells 148. However, as also detailed below, in other embodiments, various features may be provided to capture air bubbles within the wells to achieve an appropriate percentage of capacity occupied by the liquid sample.

Other suitable numbers, arrangements, and/or configurations of the wells 144, 146, 148 of the apparatus 100 are also contemplated, depending on a particular purpose. Further, a reduced thickness at the base of any or all of the wells 144, 146, 148 (or the bases of any or all of the wells of any other suitable sample tray) may be provided to increase permeability without compromising structural stability of the wells 144, 146, 148.

It has been found that capturing air or air bubbles within some or all of the wells of a sample tray helps optimize bacterial growth with respect to many bacteria to be detected. In particular, the percentage by volume of liquid sample within each well (or some of the wells) may be in the range of about 50% to about 65% (about 50% to about 65% capacity), while the remaining about 35% to about 50% percentage by volume is occupied by air and/or air bubbles. Features which may be incorporated into the wells to achieve air bubbles in this or another suitable percentage by volume range include: configuring the wells to define diamond, tear drop, or hour-glass configurations, and/or including indentations, sharp corners, protrusions, or other geometric features within any or all of the wells. Other additional or alternative features for this purpose and configured for use with the apparatus 100, 200 (FIG. 1B), or any other suitable sample testing apparatus, are detailed below with respect to FIGS. 4-5B.

Figure 4A:
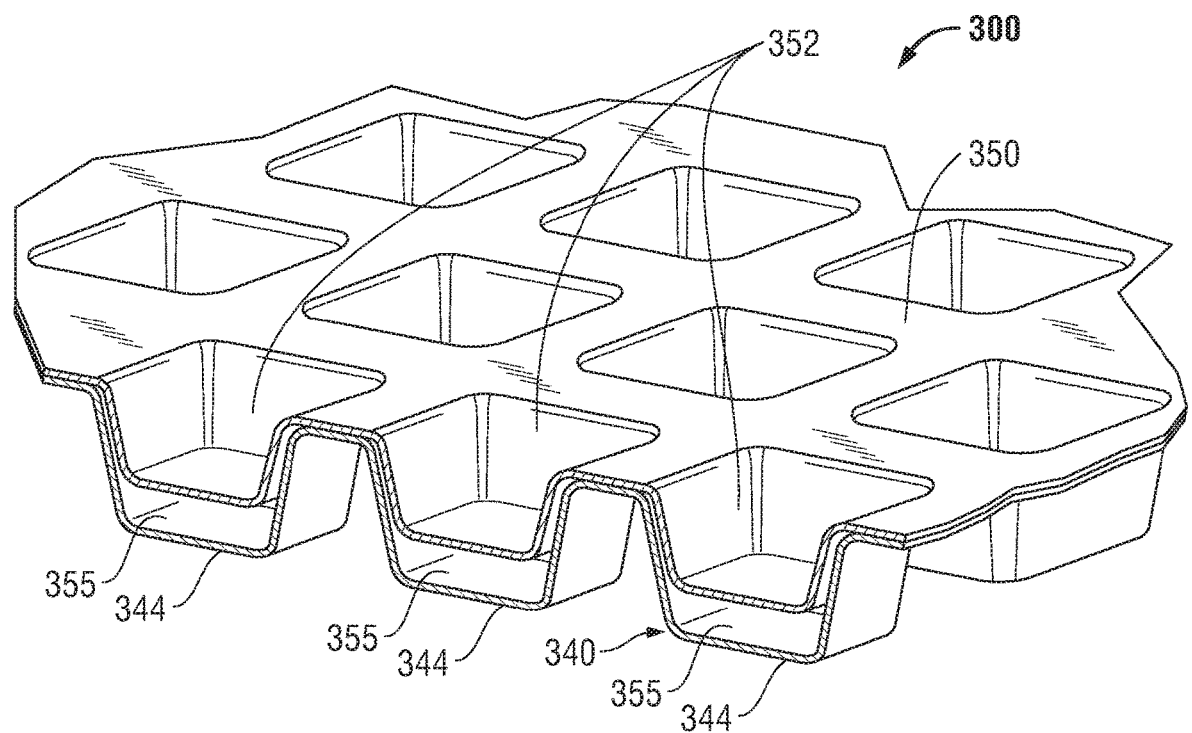
FIG. 4A is an enlarged, perspective, cut-away view of a sample tray of another multi-well sample testing apparatus, including a water-soluble film disposed thereon.

Turning to FIG. 4A, as noted above, capturing an air bubble within the sample wells has been found to help optimize bacterial growth. Accordingly, a dissolvable film 350 may be provided for positioning between the sample tray 340 and the lid member (not shown) of the apparatus 300. The apparatus 300 may be similar to the apparatus 100 (FIG. 1A) or the apparatus 200 (FIG. 1B), and may include any of the features thereof, but differs at least in that the apparatus 300 further includes the dissolvable film 350 disposed between the sample tray 340 and the lid member (not shown) thereof.

The dissolvable film 350 is dimensioned and configured similar to the sample tray 340 except that the wells 352 defined within the dissolvable film 350 define reduced depths as compared to the corresponding wells 344 of the sample tray 340. As a result of this configuration, an air pocket 355 is defined between the bases of the wells 352 of the dissolvable film 350 and the bases of the corresponding wells 344 of the sample tray 340. The dissolvable film 350 is configured to dissolve upon contact with the liquid sample without hindering the biological material to be detected or the testing medium contained within the liquid sample. As the liquid sample enters each well 344 and the dissolvable film 350 dissolves, the air disposed within the air pocket 355 is captured in the form of an air bubble within each well 344. In embodiments, the dissolvable film 350 is a water soluble film formed from polyvinyl alcohol.

Figure 4B:
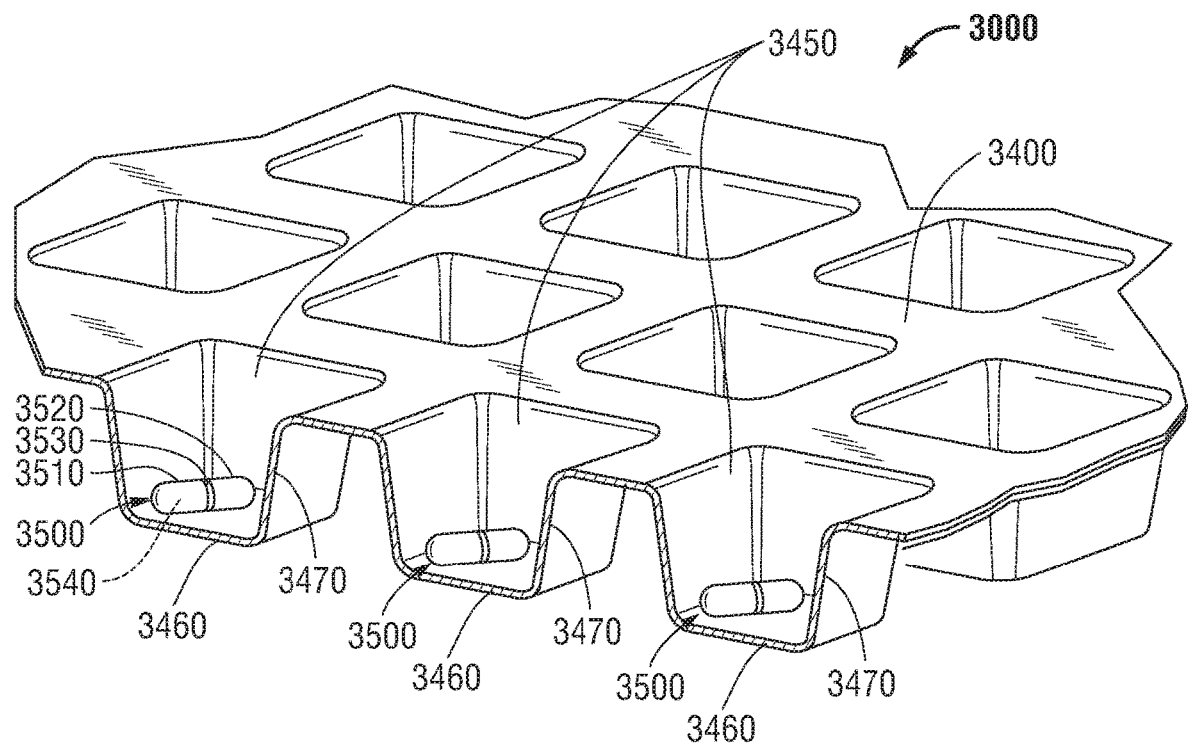
FIG. 4B is an enlarged, perspective, cut-away view of a sample tray of another multi-well sample testing apparatus, including capsules disposed within the wells thereof.

Referring to FIG. 4B, another embodiment of a sample testing apparatus 3000 is provided including a sample tray 3400 and lid member (not shown). Sample testing apparatus 3000 may be similar to apparatus 100, 200 (FIGS. 1A and 1B, respectively), or any of the other embodiments detailed herein, and may include any of the features thereof. Sample testing apparatus 3000 differs from the other embodiments detailed herein, or additionally includes, as detailed below, a dissolvable capsule 3500 disposed within one or more of wells 3450 in order to capture an air (or other gas or gas mixture) bubble within the sample well(s) 3450 to facilitate bacterial growth.

Each dissolvable capsule 3500 is configured for positioning within one of wells 3450 of sample tray 3400 and may be placed therein or adhered, e.g., using resin, to an interior surface thereof, e.g., base 3460 or any of sidewalls 3470. Capsules 3500 may be positioned and/or adhered within their respective wells 3450 during manufacturing of sample tray 3400, or may be positioned therein at the user-end. Each dissolvable capsule 3500 is formed from a dissolvable material. In embodiments, capsules 3500 are water soluble capsules such as hydroxypropyl methylcellulose (HPMC) capsules, gelatin capsules, or other suitable water soluble capsules capable of remaining substantially intact during the heat sealing process and, ultimately, sufficiently dissolving during incubation of sample testing apparatus 3000 to thereby create an air (or other gas or gas mixture) bubble within the sealed well 3450.

Each dissolvable capsule 3500 is formed from two capsule portions 3510, 3520, one of which is inserted partially into the other to define an overlapping region 3530 and an enclosed interior chamber 3540. Dissolvable capsules 3500 may be assembled from capsule portions 3510, 3520 in a normal environment to entrap air within interior chamber 3540, or may be assembled in a special environment, e.g., an oxygen-rich environment, to entrap a desired gas composition, e.g., oxygen-enriched air, within interior chamber 3540. Further, dissolvable capsules 3500 are configured so as to not interfere with the biological material to be detected or the testing medium contained within the liquid sample.

As noted above, dissolvable capsules 3500 are configured to be dissolved, e.g., via the liquid sample, to create an air (or other gas or gas mixture) bubble within the sealed well 3450. More specifically, capsules 3500 are configured, e.g., the thickness of and/or material forming capsules are selected, such that capsules 3500 begin to dissolve upon contact with the liquid sample but at a sufficiently slow rate so as to maintain the interior chamber 3540 in a sealed condition during heat sealing. Ultimately, during incubation, capsules 3500 are sufficiently dissolved so as to enable the escape of the air and/or gas(es) from interior chamber 3540 into the sealed well 3450 to provide an air (or other gas or gas mixture) bubble therein.

Figure 5A:
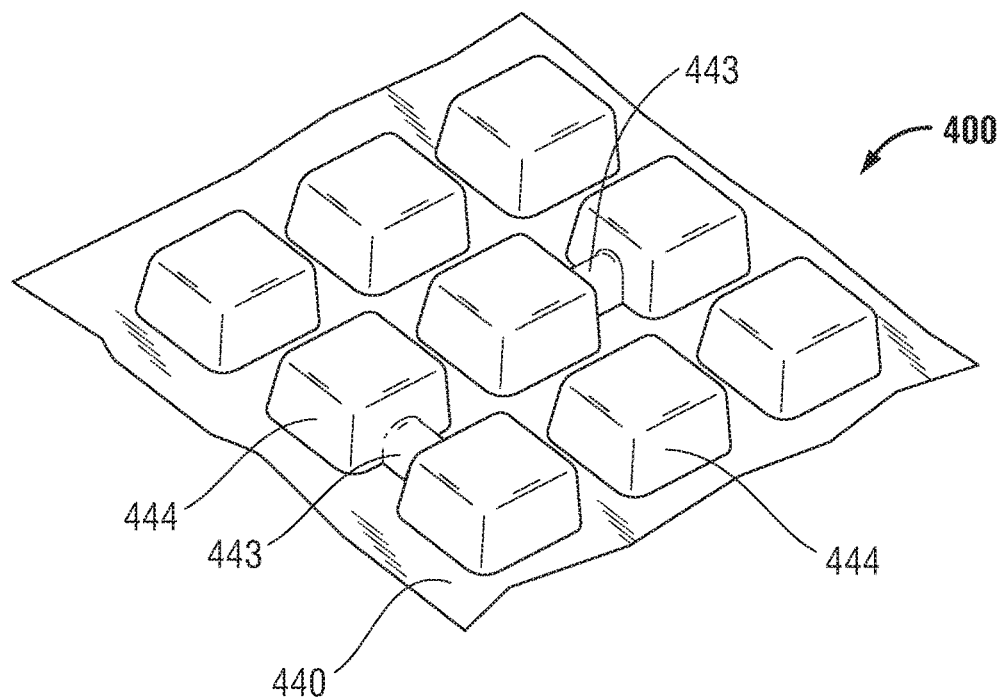
FIG. 5A is an enlarged, perspective, cut-away view of a sample tray of another multi-well sample testing apparatus, including a bridge connecting adjacent wells to one another.
Figure 5B:
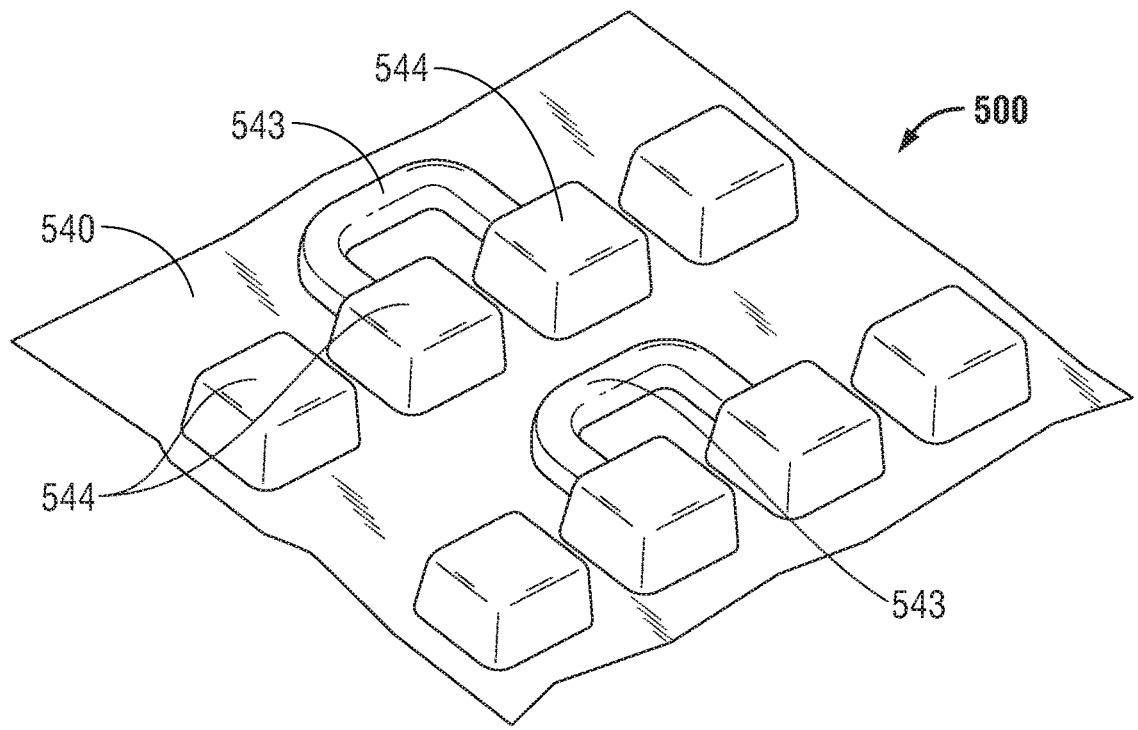
FIG. 5B is an enlarged, perspective, cut-away view of a sample tray of another multi-well sample testing apparatus, including another bridge connecting adjacent wells to one another.

With reference to FIGS. 5A-5B, as shown with respect to apparatus 400, 500, air bubbles may also be captured by providing relatively shallow bridges interconnecting adjacent wells of the sample tray. For example, as shown in FIG. 5A, the sample tray 440 may include linear bridges 443 interconnecting adjacent wells 444 to one another in any suitable pattern or configuration. Alternatively, as shown in FIG. 5B, the sample tray 540 may include curved, or "U"-shaped bridges 543 interconnecting adjacent wells 544 to one another in any suitable pattern or configuration. Other configurations of bridges are also contemplated. In either configuration, the bridges 443, 543, which define reduced depths as compared to the wells 444, 544, respectively, facilitate capturing air bubbles in the wells 444, 544 during sealing. Alternatively, a mask can be used to fully enclose one of the two interconnected wells, thereby trapping air in the enclosed well, leaving the partner well open to fill with fluid.

Figure 6A:
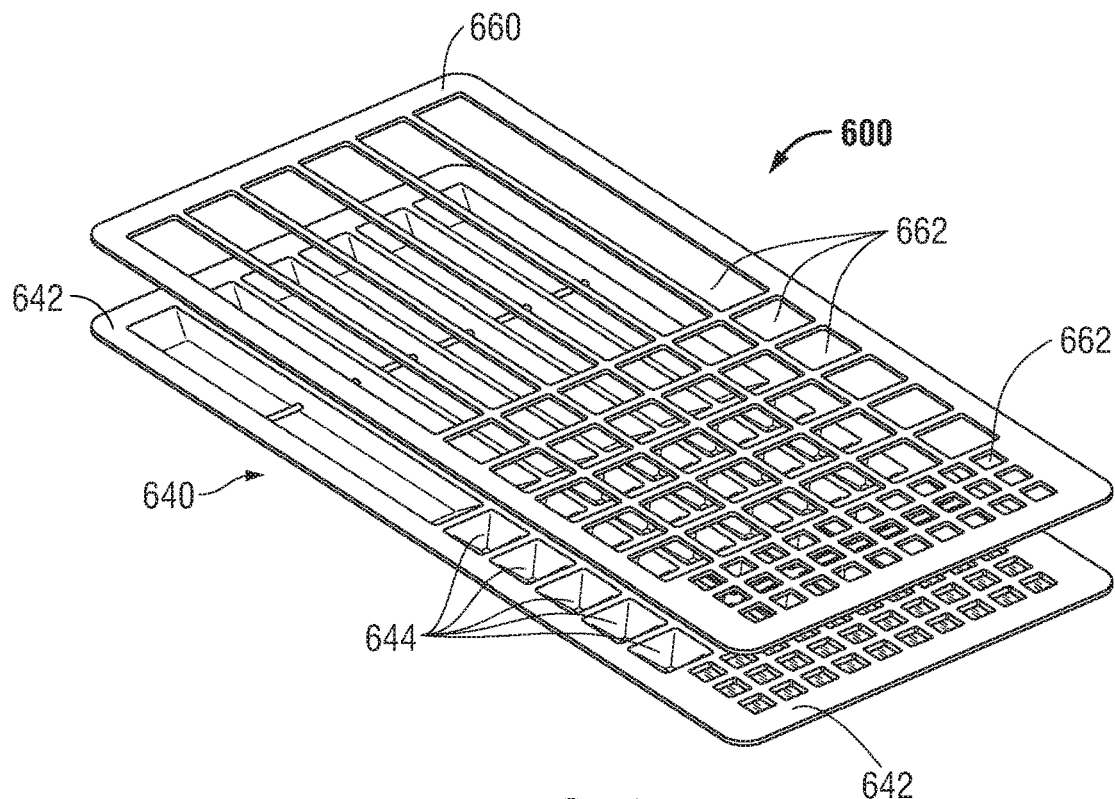
FIG. 6A is an exploded, perspective view of a sample tray of another multi-well sample testing apparatus, including a mask disposed thereon.
Figure 6B:
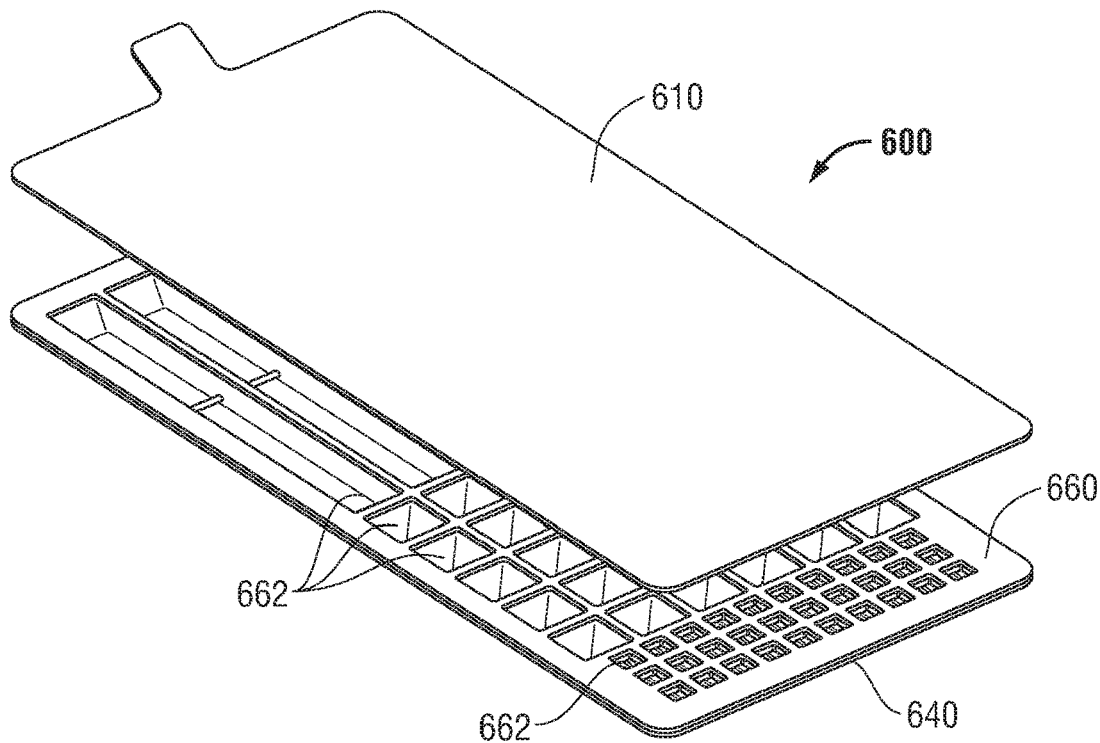
FIG. 6B is an exploded, perspective view of the sample tray and mask of FIG. 6A including a lid member disposed thereon.

Referring to FIGS. 6A-6B, as shown with respect to apparatus 600, air bubbles may also be captured by controlling the flow of the liquid sample into the wells using a mask plate 660 positioned between the lid member 610 and the sample tray 640. The mask plate 660 is dimensioned similar to the generally planar upper surface 642 of the sample tray 640 and includes a plurality of cut-outs 662, each of which corresponds to one of the wells 644 formed within the sample tray 640. However, although the cut-outs 662 are generally aligned with their corresponding wells 644, the cut-outs 662 preferably define a reduced opening in at least one dimension, e.g., the length and/or width dimension, as compared to the opening of the corresponding wells 644. This configuration creates a bottleneck effect and enables the capture of air bubbles within each of the wells 644 as the liquid sample flows through the reduced-dimension cut-outs 662 and into the relatively larger-dimensioned wells 644.

Referring generally to FIGS. 1A and 2-3B, the use of apparatus 100 for quantifying a bacterial concentration in a liquid sample is detailed. As noted above, apparatus 200, 300, 400, 500, 600 (FIGS. 1A, 4, 5A, 5B, and 6A-6B, respectively) are similar to and may include any of the features of apparatus 100, and vice versa. Accordingly, the use thereof is similar to that of apparatus 100 and will not be detailed hereinbelow for purposes of brevity.

Initially, a suitable testing medium, selected based upon the biological material to be detected, is introduced into the liquid sample and 100 mL of the liquid sample, including the testing medium, is measured. The measured 100 mL of liquid sample is then introduced, e.g., poured, into the pouch of the apparatus 100 through the open end 108 thereof. To facilitate the introduction of the liquid sample, the side edges 102, 104 of the apparatus 100 may be squeezed towards one another to slightly bend the lid member 110 and/or the sample tray 140 to enlarge the pouch opening defined between the lid member 110 and the sample tray 140.

With the liquid sample disposed within the pouch between the lid member 110 and the sample tray 140, the apparatus 100, lead by open end 108, may be fed into a heat sealer (e.g., a heat sealer sold under the name Quanti-Tray® Sealer 2×, manufactured by IDEXX Laboratories, Inc. of Westbrook, Me., USA). As the apparatus 100 is translated through the heat sealer, the heat sealer urges the lid member 110 into contact with the sample tray 140 such that the liquid sample is first evenly distributed into the small wells 144 at a full capacity volume of 0.20 mL, is then evenly distributed into the medium wells 146 at a full capacity volume of 1.01 mL, and the remaining liquid is evenly distributed into the large wells 148 (about 10.95 mL of liquid sample in each of the large wells 148 filling these large wells to about 58% capacity (or between about 50% and about 65% capacity, depending on a particular purpose). The air filling the remainder of these large wells 148 after sealing facilitates bacterial growth in these wells 148, similarly as detailed above with respect to the capture of air bubbles.

Simultaneously with or near-simultaneously with the urging of the lid member 110 and the sample tray 140 into contact with one another to distribute the liquid sample, heat applied to the apparatus 100 via the heat sealer effects heat-sealing of the adhesive layer 112 to the sample tray 140 fully about the surface 142 of the sample tray 140 to sealingly enclose each of the wells 144, 146, 148. The insulative properties of the paper backing layer 116 of the lid member 110 enable heat sealing of the adhesive layer 112 with the sample tray 140 but inhibit the liquid sample from being significant effected, i.e., heat sealing is effected with minimal temperature increase of the liquid sample.

Once the apparatus 100 has been sealed, it is incubated for a pre-determined amount of time under pre-determined conditions (depending upon the test being performed). In embodiments, the apparatus 100 (or other suitable apparatus) is incubated in an inverted orientation. This configuration allows the liquid sample within each of the wells 144, 146, 148 to directly contact and sit atop the lid member 110, while any air trapped in the wells, e.g., large wells 148, is positioned between the liquid sample and the base of the well 148. This configuration has been found to contribute to better bacteria growth. However, other incubation orientations are also contemplated.

After the incubation period, the results are determined, recorded, and analyzed. In embodiments where the paper backing layer 116 of the lid member 110 is removable, the paper backing layer 116 may be removed prior to incubation, to increase permeability, or after incubation, to facilitate determining the results. In order to determine the quantity of the biological material being tested for in the liquid sample, the number of "positive" wells are counted, as indicated by a color change or other sensible change in the well, and routine statistical analysis is performed (or a look-up table including pre-calculated statistical results of such is utilized).

Turning now to FIGS. 7A-10C, various additional embodiments of multi-well sample testing apparatus provided in accordance with the present disclosure are shown and described. Although shown as separate embodiments to highlight particular features of each of the apparatus, it is contemplated that any of features of the below embodiments be utilized in conjunction with one another and/or any of the features of the above embodiments, except where specifically contradicted.

Figure 7A:
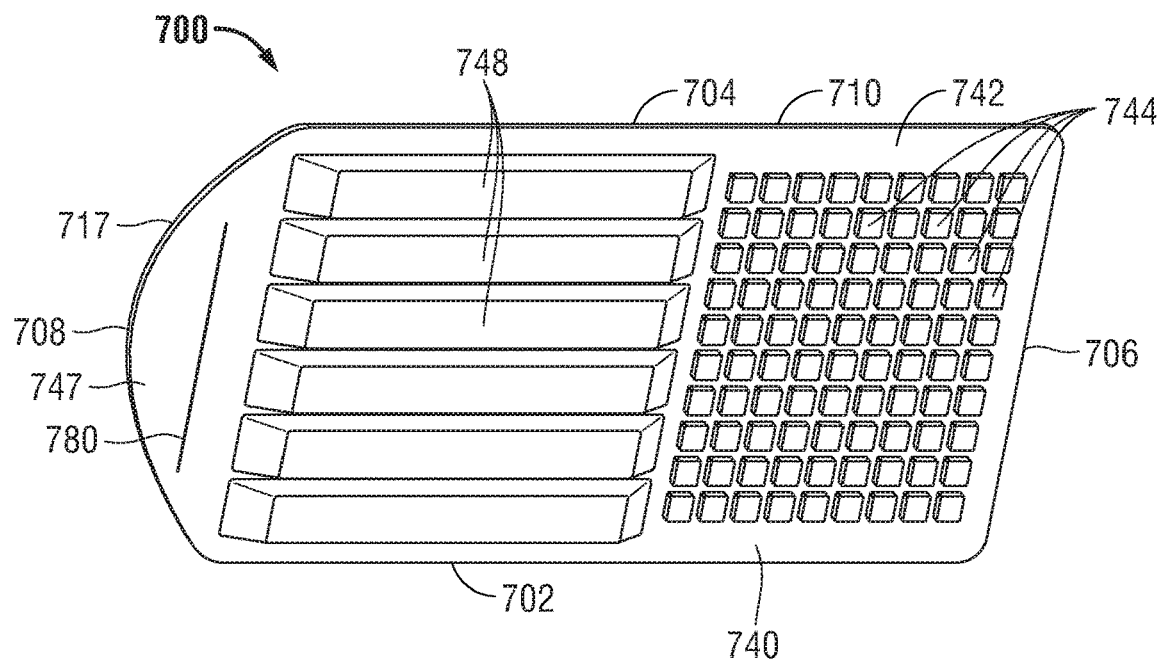
FIG. 7A is a bottom, perspective view of another multi-well sample testing apparatus provided in accordance with the present disclosure and disposed in a closed condition.
Figure 7B:
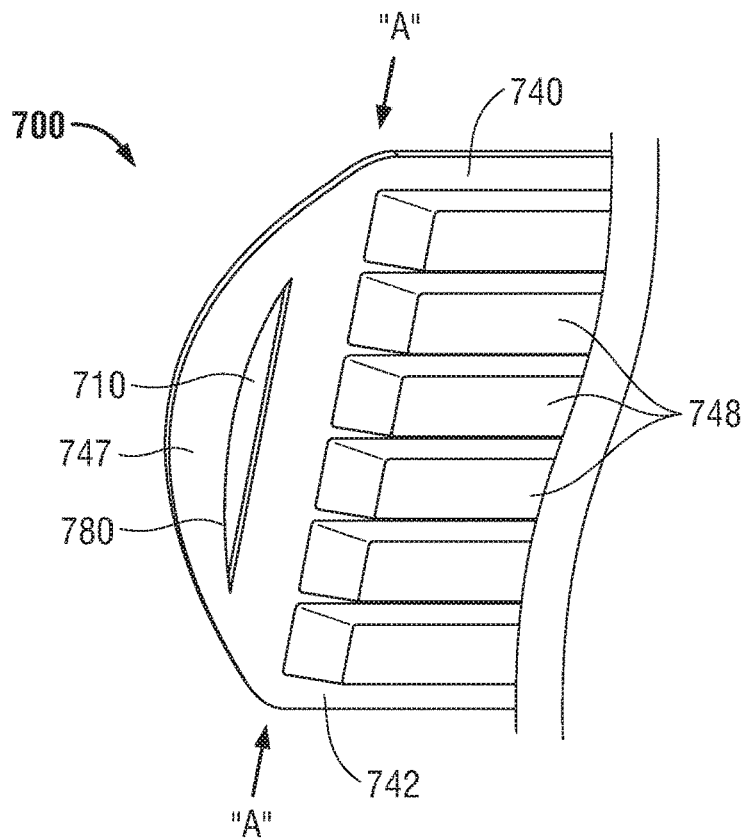
FIG. 7B is a partial, bottom, perspective view of a the apparatus of FIG. 7A, disposed in an open condition.

Referring to FIGS. 7A and 7B, multi-well sample testing apparatus 700 generally includes a lid member 710 and a sample tray 740. The lid member 710 and sample tray 740 define generally rectangular configurations of similar dimensions, except that the lid member 710 and sample tray 740 both define similar outwardly-bowed top portions 717, 747, respectively. The outwardly-bowed top portions 717, 747 facilitate the grasping and manipulation of the apparatus 700 and, as detailed below, the opening of apparatus 700 to permit the introduction of the liquid sample to be tested therein.

The lid member 710 and sample tray 740 are sealingly engaged to one another along all four outer peripheral edges of the apparatus 700, e.g., side edges 702, 704, bottom edge 706, and top edge 708, such that the outer periphery of the apparatus 700 is fully sealed. This is in contrast to apparatus 100, 200 (FIGS. 1A and 1B, respectively), detailed above, wherein only three of the edges are sealed. Rather than providing an open edge to permit introduction of the liquid sample into the interior of the apparatus 700, the apparatus 700 includes a slit 780 defined within and extending through the planar upper surface 742 of the outwardly-bowed top portion 747 of the sample tray 740, as will be detailed below. The lid member 710 may otherwise be configured similarly as any of the other embodiments detailed herein and may include any of the features and/or combination of features thereof.

The sample tray 740 of the apparatus 700 defines a generally planar upper surface 742 and includes two sets of wells 744, 748 of different configurations recessed relative to the generally planar upper surface 742. More specifically, the sample tray 740 includes a plurality of small wells 744, e.g., a 9×10 matrix of small wells 744, positioned towards the bottom edge 706 of the apparatus 700, and a plurality of elongated large wells 748, e.g., six elongated large wells 748, extending longitudinally between the small wells 744 and outwardly-bowed top portion 747 of the sample tray 740. The small wells 744 are configured to be filled with the liquid sample to 100% capacity with the remainder of the sample being distributed into (but not filling) the elongated large wells 748. Other configurations of wells of similar and/or varying configuration are also contemplated, such as those detailed above.

Continuing with reference to FIGS. 7A and 7B, the sample tray 740, as mentioned above, includes a slit 780 defined within and extending through the outwardly-bowed top portion 747 of the sample tray 740 for introduction of the liquid sample into the interior pouch of the apparatus 700. Although the slit 780 extends through the sample tray 740 (to provide access to the interior pouch of the apparatus 700), the slit 780 does not penetrate or extend into the lid member 710 such that the slit 780 is the only access point for introducing the liquid sample into the interior pouch of the apparatus 700. The slit 780 may be formed via laser-cutting or in any other suitable fashion.

In use, the liquid sample, e.g., a 100 mL liquid sample including the testing medium, is poured into the interior pouch of the apparatus 700 through the slit 780. In order to introduce the liquid sample, the apparatus 700 is squeezed inwardly from the opposite side edges 702, 704 thereof adjacent the outwardly-bowed top portion 747 to flex, or bend the sample tray 740 (as indicated by arrows "A") to define an arcuate configuration. In this configuration, the slit 780 is enlarged and a space is established between the sample tray 740 and the lid member 710 to enlarge the interior pouch opening defined by the slit 780. Alternatively, while grasping the apparatus 700, the outwardly-bowed top portion 747 of the sample tray 740 may be manipulated, e.g., bent, relative to the remainder of the sample tray 740 to likewise enlarge the interior pouch opening defined via the slit 780.

With the liquid sample disposed within the interior pouch of the apparatus 700, the apparatus 700 may be fed into a heat sealer which urges the lid member 710 into contact with the sample tray 740 such that the liquid sample is first evenly distributed into the small wells 744 at full capacity, and such that the remainder of the liquid sample is evenly distributed into the large wells 748. The large wells 748 are only partially filled, however, with the remaining portions of the large wells 748 occupied by air. Simultaneously with or near-simultaneously with the urging of the lid member 710 and the sample tray 740 into contact with one another to distribute the liquid sample, heat applied to the apparatus 700 via the heat sealer effects heat-sealing of the lid member 710 to the sample tray 740 to sealingly enclose each of the wells 744, 748. Incubation, result determination, and analysis may be performed similarly as detailed above.

Figure 8:
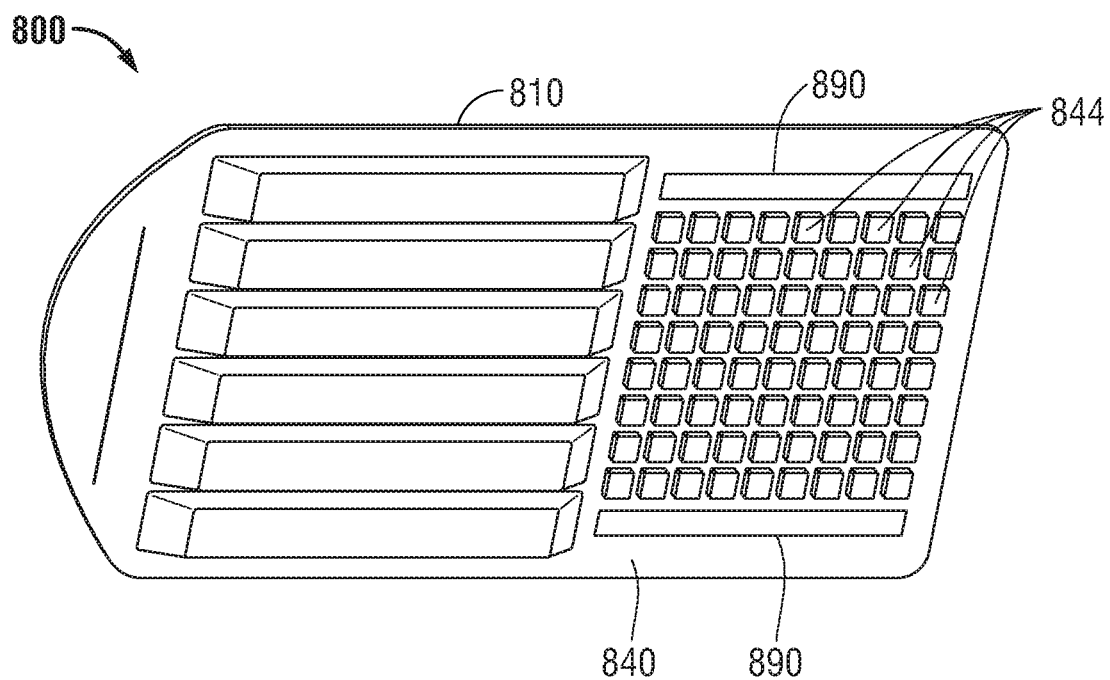
FIG. 8 is a bottom, perspective view of another multi-well sample testing apparatus provided in accordance with the present disclosure.

Referring to FIG. 8, multi-well sample testing apparatus 800 is similar to the apparatus 700 (FIGS. 7A and 7B) and generally includes a lid member 810 and a sample tray 840. However, in contrast to the apparatus 700 (FIGS. 7A and 7B), the sample tray 840 of the apparatus 800 includes a pair of reinforcement ribs 890 extending longitudinally on either side of the small wells 844. Room for accommodating the reinforcement ribs 890 may be provided by removing the outer-most rows of small wells 844 on either side of the matrix, thus forming a 9×8 matrix of the small wells 844. However, other suitable configurations, with or without removing rows of wells, are also contemplated. The reinforcement ribs 890 may be formed integrally with the sample tray 840, e.g., providing an increased thickness to form the reinforcement ribs 890. Alternatively, the reinforcement ribs 890 may be formed from any suitable material, e.g., stainless steel, polymeric materials, etc., and may be embedded within the sample tray 840, disposed on the interior or exterior-facing surface of the sample tray 840, disposed on the interior or exterior-facing surface of the lid member 810, or secured to the apparatus 800 in any other suitable fashion. The reinforcement ribs 890 provide structural support to the apparatus 800 and inhibit twisting and other such manipulation of the apparatus 800. The reinforcement ribs 890 also help maintain proper positioning of the apparatus 800 during insertion into and use of the heat sealer to seal the apparatus 800, thus helping to ensure an effective seal. The configuration and use of the apparatus 800 is otherwise similar to that of the apparatus 700 (FIGS. 7A and 7B).

Figure 9:
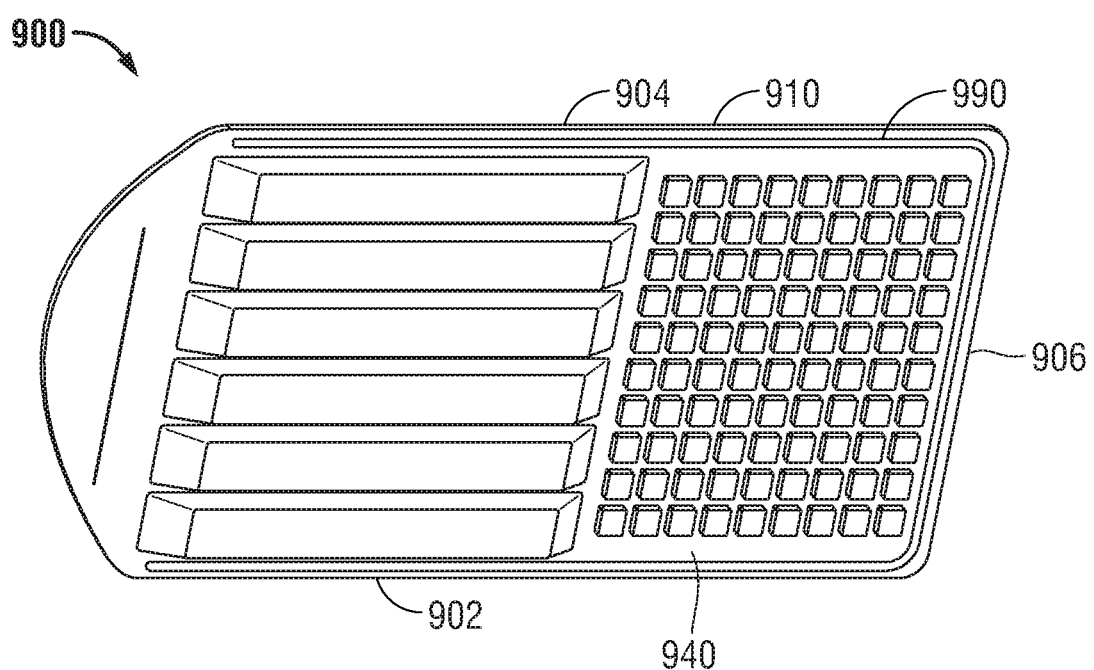
FIG. 9 is a bottom, perspective view of another multi-well sample testing apparatus provided in accordance with the present disclosure.

Referring to FIG. 9, multi-well sample testing apparatus 900 is similar to the apparatus 700, 800 (FIGS. 7A-7B and 8, respectively) and generally includes a lid member 910 and a sample tray 940. The apparatus 900 differs from the apparatus 800 (FIG. 8) in the reinforcement thereof. More specifically, rather than providing the reinforcement ribs 890 as in the apparatus 800 (see FIG. 8), the apparatus 900 includes an elongated, generally U-shaped reinforcement member 990 extending about three perimeter edges of the sample tray 940, e.g., the first and second side edges 902, 904, respectively, and the bottom edge 906. The reinforcement member 990 may be formed integrally with the sample tray 940, e.g., providing an increased thickness to form the reinforcement member 990. Alternatively, the reinforcement member 990 may be formed as a wire or cable made from any suitable material, e.g., stainless steel, polymeric materials, etc., and may be embedded within the sample tray 940, disposed on the interior or exterior-facing surface of the sample tray 940, disposed on the interior or exterior-facing surface of the lid member 910, or secured to the apparatus 900 in any other suitable fashion. The reinforcement member 990 provides structural support to the apparatus 900 and inhibits twisting and other such manipulation of the apparatus 900. Further, the reinforcement member 990 helps maintain proper positioning of the apparatus 900 during insertion into and use of the heat sealer to seal the apparatus 900, thus helping to ensure an effective seal. The configuration and use of the apparatus 900 is otherwise similar to that of the apparatus 700 (FIGS. 7A and 7B).

Figure 10C:
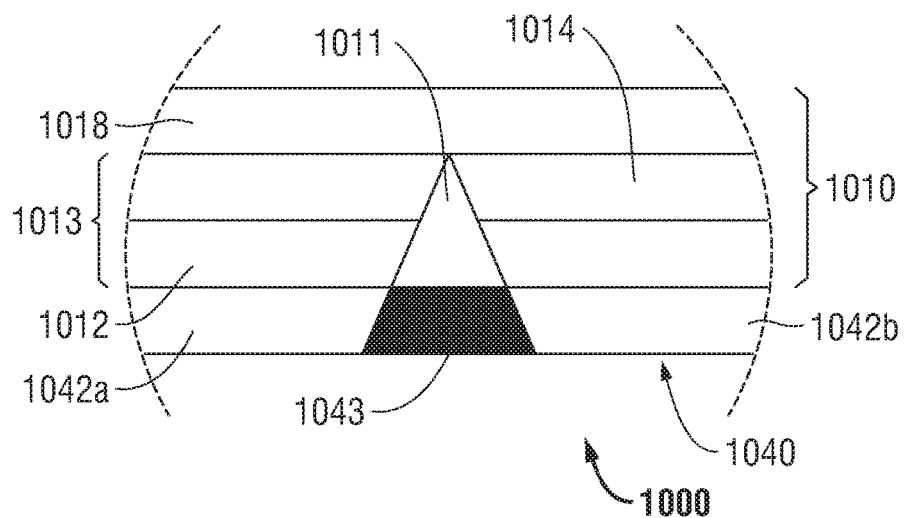
FIG. 10C is an enlarged view of the area of detail indicated as "10C" in FIG. 10B.

Turning to FIGS. 10A-10C, multi-well sample testing apparatus 1000 is similar to the apparatus 700 (FIGS. 7A and 7B) and generally includes a lid member 1010 and a sample tray 1040, which may include any of the features of any of the other embodiments detailed herein, and/or combinations thereof. The lid member 1010 and sample tray 1040 of the apparatus 1000 define generally rectangular configurations of similar dimensions, except that the lid member 1010 and sample tray 1040 both define outwardly-bowed top portions 1017, 1047, respectively.

The lid member 1010 of the apparatus 1000, more specifically, is formed from a plurality of layers: an adhesive layer 1012, a breathable film layer 1014, and a release liner 1018. The adhesive and breathable film layers 1012, 1014, respectively, may be configured similarly to those detailed above with respect to the lid member 110 of the apparatus 100 (FIG. 1A). Exemplary embodiments of release liners will be described in greater detail below with reference to FIGS. 11 and 12. The release liner 1018 is secured to the remainder of the lid member 1010 in any suitable manner that permits the release liner 1018 to be peeled off of or otherwise removed from the remainder of the lid member 1010, e.g., the release liner 1018 may be secured to the remainder of the lid member 1010 via casting, laminating, adhering, etc.

The apparatus 1000 defines a perforation 1011 that extends through the outwardly-bowed top portion 1047 of the sample tray 1040 and partially through the outwardly-bowed top portion 1017 of the lid member 1010. More specifically, the perforation 1011 extends through the adhesive and breathable film layers 1012, 1014 of the lid member 1010, but not into the release liner 1018. The perforation 1011 defines a wedge-shape configuration that is wider adjacent the sample tray 1040 and progressively decreases in width as the perforation 1011 extends further through the sample tray 1040 and into the adhesive and breathable film layers 1012, 1014 of the lid member 1010, although other configurations are also contemplated. The perforation 1011 may be formed via kiss-cutting, or other suitable process.

Despite the perforation 1011 extending through the outwardly-bowed top portion 1047 of the sample tray 1040, the sample tray 1040 includes one or more connectors 1043 extending between and interconnecting the portions 1042a, 1042b of the sample tray 1040 that are separated via the perforation 1011. Connectors 1043 are formed integrally with the portions 1042a, 1042b of the sample tray 1040 and retain the portions 1042a, 1042b of the sample tray 1040 in a generally planar configuration. As detailed below, the connectors 1043 are capable of being snapped, or broken to permit removal of the portion 1042a of the sample tray 1040 and a portion 1013 of the lid member 1010, thereby facilitating removal of the release liner 1018 from the apparatus 1000. Further, the portion of sample tray 1040 adjacent perforation 1011 (including connectors 1043) may define a rigid or more-rigid configuration to facilitate snapping, or breaking of connectors 1043. As shown in FIG. 10A, two connectors 1043, one disposed towards each side of the apparatus 1000, are provided, although other configurations are also contemplated.

Similarly as detailed above with respect the apparatus 700 (FIGS. 7A and 7B), the lid member 1010 and sample tray 1040 of the apparatus 1000 are sealingly engaged to one another along all four outer peripheral edges of the apparatus 1000. However, rather than providing a separate slit, the portion of the perforation 1011 extending between the connectors 1043 serves as the selectively enlargeable slit that permits introduction of the liquid sample into the interior of the apparatus 1000.

In use, to introduce a liquid sample into the interior pouch defined by the apparatus 1000, similarly as detailed above, the apparatus 1000 is squeezed inwardly from the opposite side edges thereof adjacent the perforation 1011 to flex, or bend the sample tray 1040 and enlarge the spacing between the sample tray 1040 and lid member 1010 adjacent the perforation 1011. As a result, the access opening to the interior pouch defined between the sample tray 1040 and lid member 1010 is enlarged, facilitating introduction of the liquid sample into the interior of the apparatus 1000.

Once the liquid sample has been introduced into the apparatus 1000, the apparatus 1000 may be sealed using a heat sealer. During heat sealing, the release liner 1018 serves as an insulator to limit the amount of heat conducted to the remainder of the lid member 1010 and/or other portions of the apparatus 1000, thereby protecting the apparatus 1000 from heat-damage and ensuring formation of an effective seal. Thereafter, the release liner 1018 is removed and the apparatus 100 is incubated. Alternatively, the release liner 1018 may be removed prior to heat sealing.

In order to remove the release liner 1018, the user grasps the body of the apparatus 1000 with one hand, and the outwardly-bowed top portions 1047, 1017 of the sample tray 1040 and the lid member 1010 with the other hand, and bends the outwardly-bowed-top portions 1047, 1017 back onto the body portion of the apparatus 1000. The perforation 1011 serves as the hinge point for the bending of the outwardly-bowed-top portions 1047, 1017 relative to the body portion of the apparatus 1000 and, upon sufficient bending, connectors 1043, which extend across the perforation 1011, are snapped or broken, thereby separating the portions 1042a, 1042b of the sample tray 1040 from one another. The snapping or breaking of connectors 1043 also decouples the portion 1013 of the adhesive and breathable film layers 1012, 1014 of the lid member 1010 from the remainder, e.g., the body, of the lid member 1010. However, as the release liner 1018 is not interrupted by the perforation 1011, the release liner 1018 remains intact.

With the portions 1042a, 1013 of the sample tray 1040 and lid member 1010, respectively, separated from the portion 1042b and body portion of the lid member, respectively (except for the release liner 1018), the portions 1042a, 1013 may be further pulled back towards the opposite end of the apparatus 1000 to peel the release liner 1018 off of the remaining, e.g., the body, of the lid member 1010. Once the release liner 1018 (along with the portions 1042b and 1013) have been peeled-off and removed, incubation, result determination, and analysis may be performed similarly as detailed above.

Figure 11:
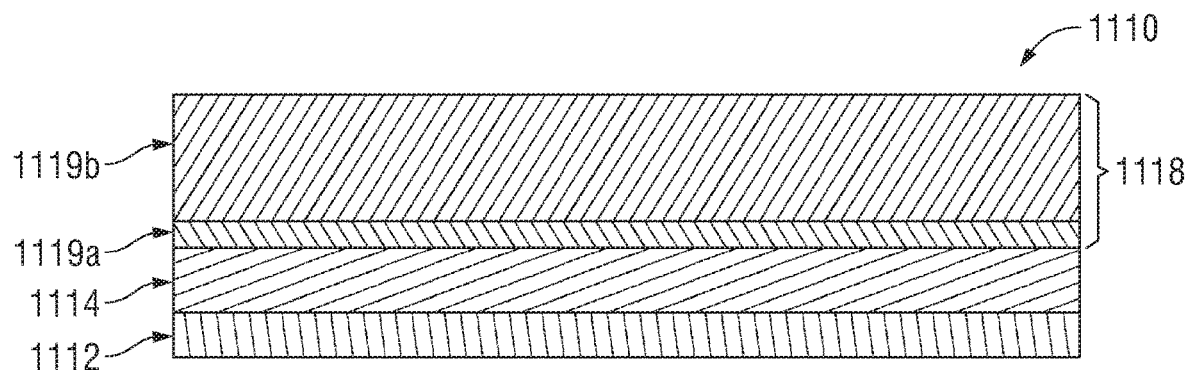
FIG. 11 is a transverse, cross-sectional view of a portion of another lid member provided in accordance with the present disclosure and including a release liner.

Turning now to FIG. 11, an embodiment of a lid member 1110 incorporating a release liner 1118 and configured for use with the apparatus 1000 (FIGS. 10A-10C), or any other suitable apparatus, is shown. The lid member 1110 includes an adhesive layer 1112, a breathable film layer 1114, and a release liner 1118. The adhesive layer 1112 and breathable film layer 1114 may be configured similarly as any of the above-detailed embodiments, and may be joined via co-extrusion, or other suitable process. The release liner 1118 includes a relatively thin silicone layer 1119a, and a relatively thick clay-coated paper layer 1119b disposed on the silicone layer 1119a. The silicone layer 1119a allows for the initial retention of the release liner 1118 about the adhesive and breathable film layers 1112, 1114, but also facilitates the removal therefrom upon peeling of the release liner 1118. The breathable film layer 1114 is extruded directly onto the silicone layer 1119a of the release liner 1118 and the adhesive layer 1112 is extruded directly onto the breathable film layer 1114. Alternatively, the breathable film layer 1114 and the adhesive layer may be co-extruded directly onto the release liner 1118.

Figure 12:
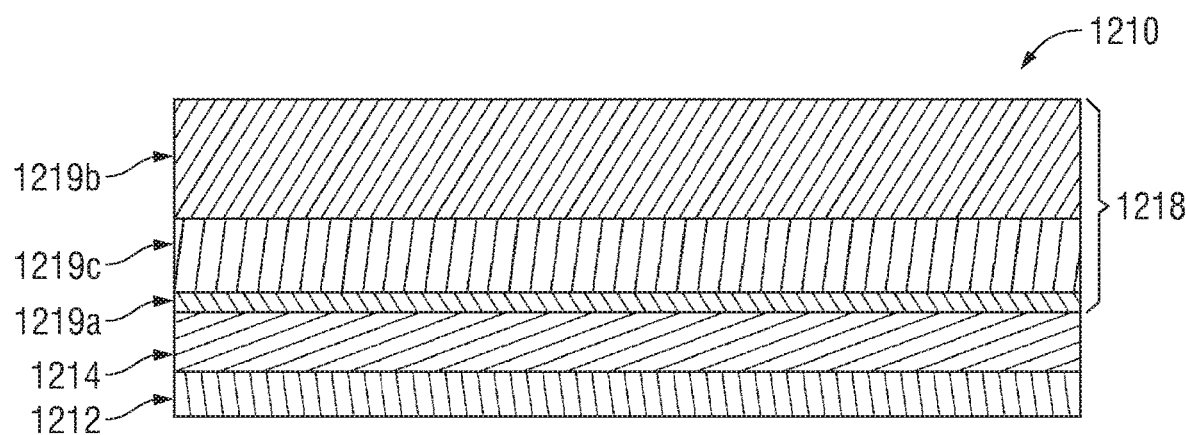
FIG. 12 is a transverse, cross-sectional view of a portion of another lid member provided in accordance with the present disclosure and including a release liner.

FIG. 12 illustrates another embodiment of a lid member 1210 incorporating a release liner 1218 and configured for use with the apparatus 1000 (FIGS. 10A-10C), or any other suitable apparatus. The lid member 1210 includes an adhesive layer 1212, a breathable film layer 1214, and a release liner 1218. The adhesive layer 1212 and breathable film layer 1214 may be configured similarly as any of the above-detailed embodiments, and may be joined via co-extrusion, or other suitable process. The release liner 1218 includes a relatively thin silicone layer 1219a, a relatively thick clay-coated paper layer 1219b, and a polyester layer 1219c having a thickness less than that of the clay-coated paper layer 1219b but greater than that of the silicone layer 1219a. The breathable film layer 1214 is extruded directly onto the silicone layer 1219a of the release liner 1218 and the adhesive layer 1212 is extruded directly onto the breathable film layer 1214. Alternatively, the breathable film layer 1214 and the adhesive layer 1212 may be co-extruded directly onto the release liner 1218. Further, the silicone, clay-coated paper, and polyester layers 1219a, 1219b, 1219c may be coupled to one another via laminating, or other suitable process.

Referring generally to FIGS. 13A-16D, and as mentioned above, the various apparatus detailed herein are configured for use with a heat sealer to seal a portion of the liquid sample within each of the wells of the apparatus. In order to facilitate the heat sealing of the apparatus, a receptacle configured to receive the apparatus may be utilized. The receptacle maintains the apparatus in a desired orientation, inhibits bending or twisting of the apparatus, and, in conjunction with the heat sealer, guides the apparatus through the heat sealer to ensure formation of an effective seal without damaging the apparatus. Various embodiments of such receptacles are detailed below. Each of these receptacles includes a base portion and a releasably engagable cover flap.

In embodiments where the apparatus to be sealed defines a relatively thin configuration, is more prone to sticking or misalignment, and/or includes a more heat-sensitive lid member, e.g., in embodiments where a release liner is not provided, the cover flap is utilized as a protector that protects the lid member of the apparatus during heat sealing. However, in other embodiments where such concerns are minimal, e.g., where a release liner is provided or the apparatus defines a more rigid or robust configuration, the base portion of the receptacle may be utilized without the cover flap.

Referring to FIGS. 13A-13C, a receptacle 1300 is shown configured for use with an apparatus 1301. The apparatus 1301 is shown generically, as it is envisioned that any suitable apparatus, such as any of those detailed above, may be utilized in conjunction with the receptacle 1300 to facilitate sealing of the apparatus 1301 when put through a heat sealer. The receptacle 1300 includes a base portion 1320 and a cover flap 1340 that is releasably engagable with the base portion 1320. The base portion 1320 is configured to receive the apparatus 1301 therein, while the cover flap 1340 is configured to sit atop the lid member 1302 of the apparatus 1301 to enclose the apparatus 1301 within the receptacle 1300 and protect the lid member 1302 of the apparatus 1301 during heat sealing.

The base portion 1320 of the receptacle 1300 defines a generally rectangular configuration having an upper surface 1322 and a cavity 1324 recessed within the upper surface 1322. The cavity 1324 is dimensioned similarly to the apparatus 1301 and is configured to receive the apparatus 1301 therein. In some configurations, the cavity 1324 is dimensioned such that the outer peripheral edge of the apparatus 1301 serves as a lip that is seated on the upper surface 1322 of the base portion 1320 while the remainder of the apparatus 1301 is seated within the cavity 1324. The cavity 1324 may further include dividers, alignment structures, etc. (not explicitly shown) disposed therein that are configured for positioning between the wells of the apparatus 1301 to help ensure proper placement and alignment of the apparatus 1301 within the base portion 1320 of the receptacle 1300. The base portion 1320 further includes an engagement slot 1326 disposed towards an end thereof and extending transversely along a portion of the end of the base portion 1320. The engagement slot 1326 defines a shoulder 1328 configured to pivotably engage the cover flap 1340, as detailed below.

The cover flap 1340, shown in FIG. 13B, includes a generally planar body portion 1342, an engagement pin 1344, and a flange portion 1346 extending between and engaging the body portion 1342 and the engagement pin 1344 to one another. The body portion 1342 and flange portion 1346, which is integral with the body portion 1342, may be formed from a silicone-based material, or any other suitable material(s). The base portion 1320 (FIG. 13A) may likewise be formed from a silicone-based material or other suitable material(s) similar to or different from that of the cover flap 1340. The engagement pin 1344 may be formed from stainless steel or other suitable material suitable for use in a heat sealer. Further, the flange portion 1346 may be secured to the engagement pin 1344 via an adhesive, may be looped about the engagement pin 1344, or may be secured thereto in any other suitable fashion.

Referring to FIG. 13C, in order to engage the cover flap 1340 with the base portion 1320, the engagement pin 1344 of the cover flap 1340 is inserted into the engagement slot 1326 of the base portion 1320 under sufficient urging to expand the engagement slot 1326 and permit passage of the engagement pin 1344 beyond the shoulder 1328, such that the engagement pin 1344 is snapped into engagement within the enlarged-diameter portion 1329 of the engagement slot 1326 adjacent the shoulder 1328. In this position, the shoulder 1328 pivotably retains the engagement pin 1344 therein, while permitting the cover flap 1340 to pivot from an open position (FIG. 13A) for insertion and removal of the apparatus 1301 (FIG. 13A) from the base portion 1320, and a closed position, wherein the cover flap 1340 is disposed atop the lid member 1302 of the apparatus 1301 (FIG. 13A) to enclose the apparatus 1301 (FIG. 13A) within the receptacle 1300.

Figure 14:
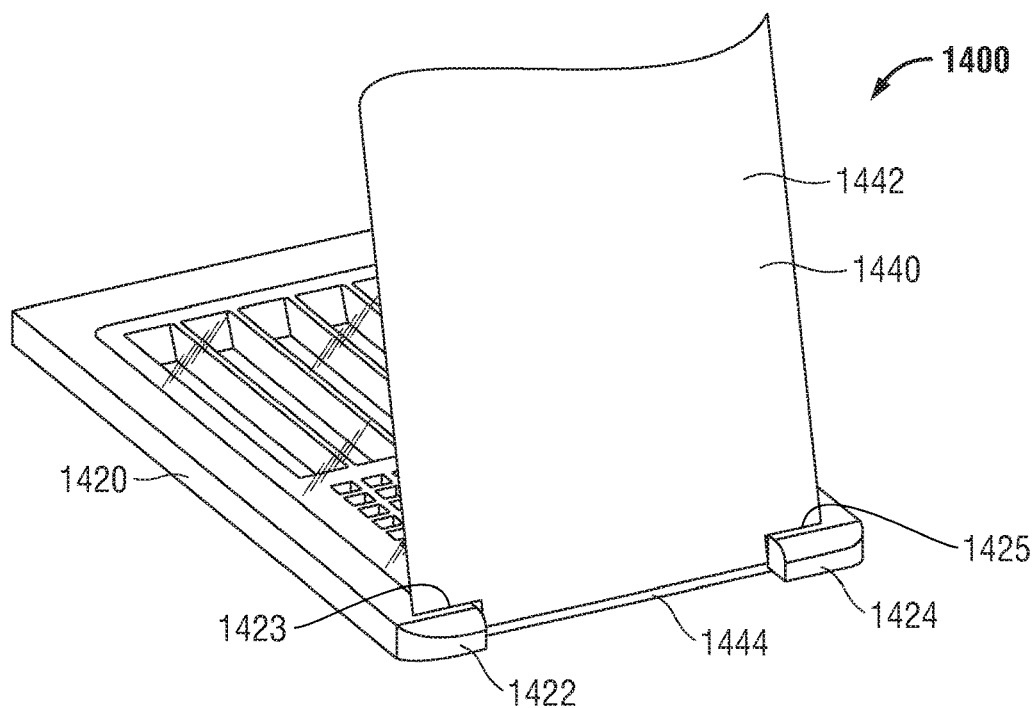
FIG. 14 is a perspective view of another sealing insert provided in accordance with the present disclosure.

Turning to FIG. 14, another embodiment of a receptacle 1400 provided in accordance with the present disclosure is shown. The receptacle 1400 includes a base portion 1420 and a cover flap 1440 and is similar to the receptacle 1300 (FIGS. 13A-13C) except for the engagement mechanism for coupling the base portion 1420 and cover flap 1440 to one another. For purposes of brevity, only such differences are detailed below.

The base portion 1420 of the receptacle 1400 includes a pair of fingers 1422, 1424 extending from an end thereof, one positioned towards each end corner of the base portion 1420. The fingers 1422, 1424 are spaced-apart from the base portion 1420 and extend towards one another to define an engagement area 1423, 1425 between the respective finger 1422, 1424 and the base portion 1420.

The cover flap 1440 includes a generally planar body portion 1442 and an engagement pin 1444 coupled to the body portion 1442, e.g., via an intermediate flange portion or directly thereto. The ends of the engagement pin 1444 are configured for receipt within the engagement areas 1423, 1425 of the base portion 1420 in pivotable, snap-fit engagement therewith to couple the cover flap 1440 to the base portion 1420.

Figure 15:
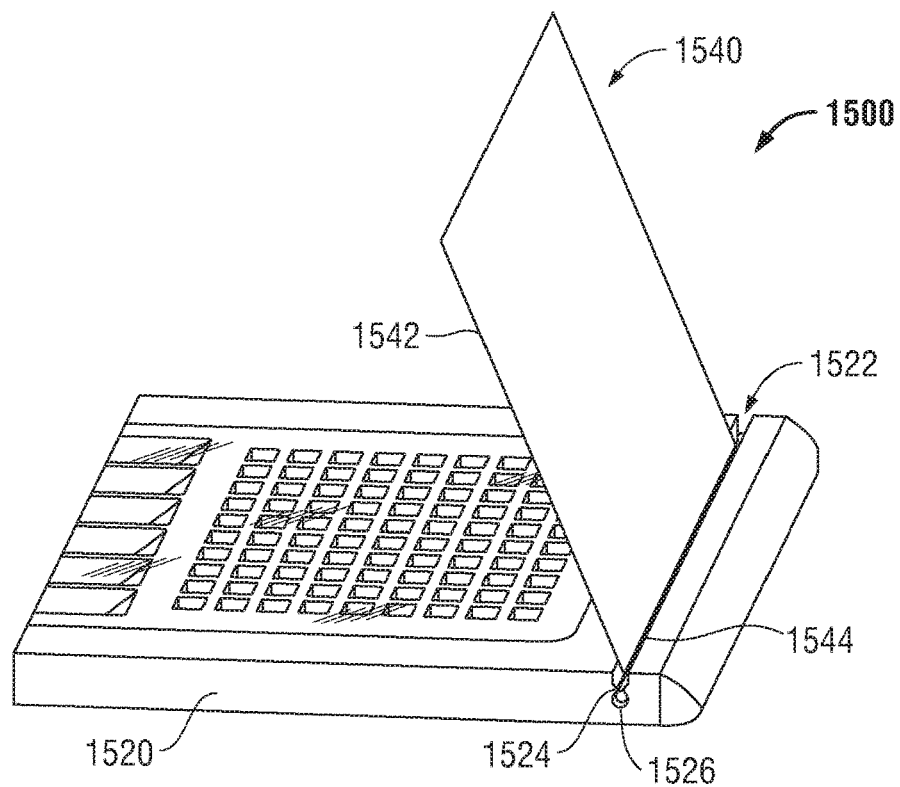
FIG. 15 is a perspective view of another sealing insert provided in accordance with the present disclosure.
Figure 16A:
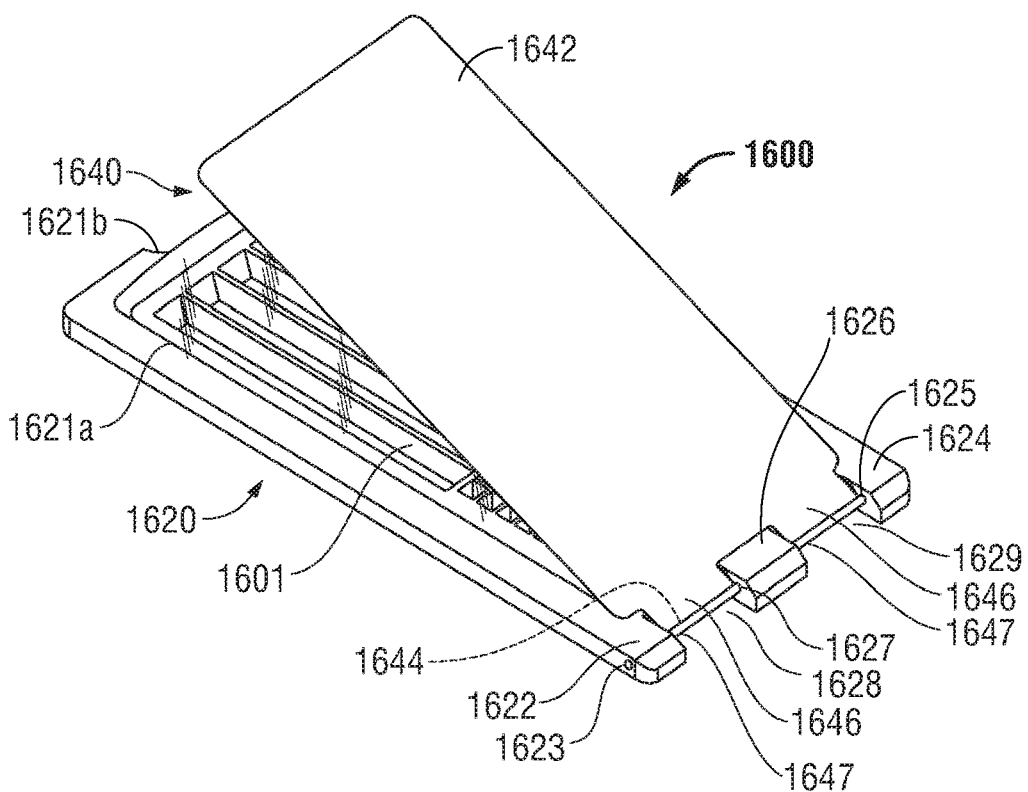
FIG. 16A is a perspective view of another sealing insert provided in accordance with the present disclosure.
Figure 16B:
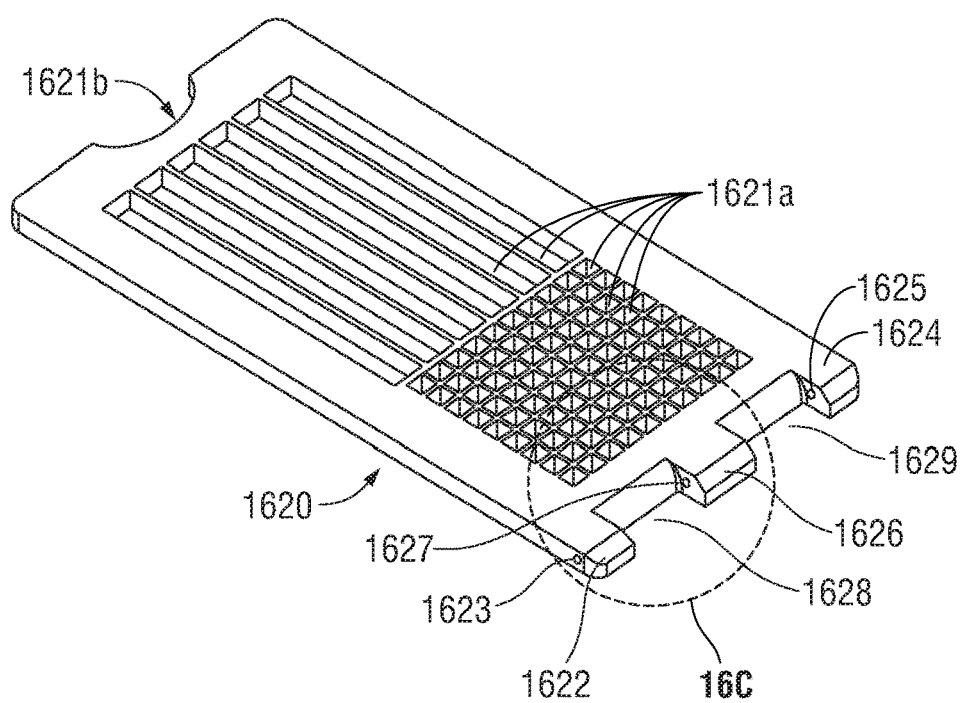
FIG. 16B is a perspective view of a base of the sealing insert of FIG. 16A.
Figure 16C:
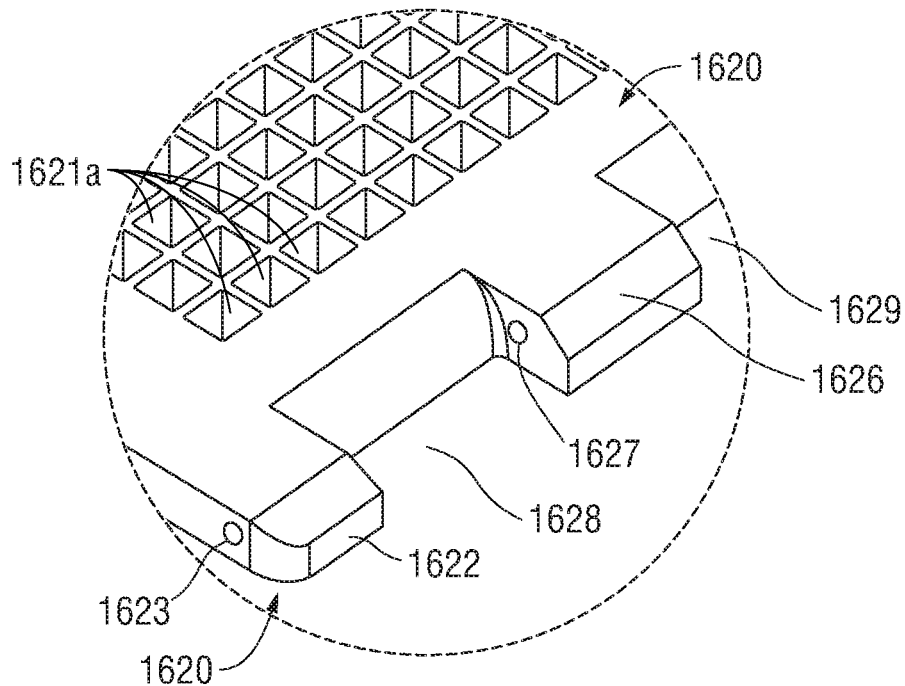
FIG. 16C is an enlarged view of the area of detail indicated as "16C" in FIG. 16B.
Figure 16D:
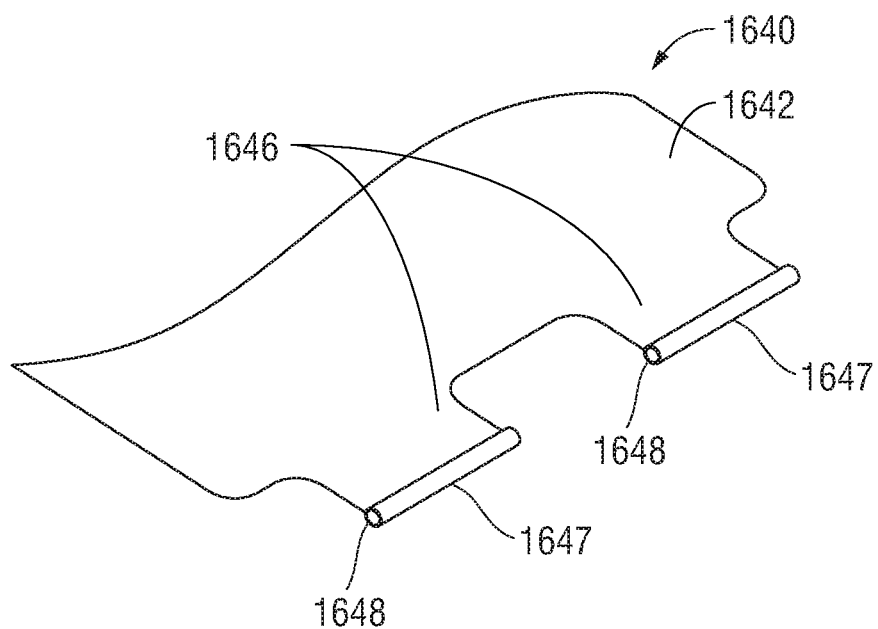
FIG. 16D is an enlarged perspective view of the engagement end of the cover of the sealing insert of FIG. 16A.

FIG. 15 illustrates another embodiment of a receptacle 1500 provided in accordance with the present disclosure. The receptacle 1500 includes a base portion 1520 and a cover flap 1540 and is similar to the receptacle 1300 (FIGS. 13A-13C) except for the engagement mechanism for coupling the base portion 1520 and cover flap 1540 to one another. For purposes of brevity, only such differences are detailed below.

The base portion 1520 of the receptacle 1500 includes a slot 1522 defined therein towards and end thereof that extends transversely across the base portion 1520. The slot 1522 includes a relatively narrow neck portion 1524 extending adjacent the mouth of the slot 1522, and a cylindrical, relatively larger diameter engagement portion 1526 extending along the nadir of the slot 1522.

The cover flap 1540 includes a generally planar body portion 1542 and an engagement pin 1544 coupled to the body portion 1542, e.g., via an intermediate flange portion or directly thereto. The engagement pin 1544 defines a generally cylindrical configuration that approximates the diameter of the cylindrical engagement portion 1526 of the slot 1522 defined within the base portion 1520 but is larger than the width of the neck portion 1524.

In order to engage the cover flap 1540 with the base portion 1520, the engagement pin 1544 of the cover flap 1540 is inserted into the slot 1522 of the base portion 1520 under sufficient urging to expand the neck portion 1524 and permit passage therethrough, ultimately such that the engagement pin 1544 is seated within the cylindrical portion 1526 of the slot 1522, thereby pivotably coupling the cover flap 1540 to the base portion 1520.

Referring to FIGS. 16A-16D, another embodiment of a receptacle 1600 provided in accordance with the present disclosure is shown. The receptacle 1600 includes a base portion 1620 and a cover flap 1640 and is similar to the receptacle 1300 (FIGS. 13A-13C) except for the engagement mechanism for coupling the base portion 1620 and cover flap 1640 to one another. For purposes of brevity, only such differences are detailed below.

The base portion 1620 of the receptacle 1600 defines a cavity having a plurality of discrete chambers 1621a arranged to define a configuration complementary to that of the apparatus 1601 configured for receipt therein such that each of the chambers 1621a receives one of the wells of the apparatus 1601. The base portion 1620 also defines a cut-out 1621b at a first end thereof that is configured to facilitate the insertion and removal of the apparatus 1601 therefrom. Although not shown, either or both of these features may be provided for use with the above-detailed receptacles.

The base portion 1620 of the receptacle 1600 further includes a plurality of spaced-apart fingers, e.g., three, spaced-apart fingers 1622, 1624, 1626, extending from the second end (the opposite end as the cut-out 1621b) thereof. As illustrated, a first finger 1622 is disposed towards one side of the base portion 1620, a second finger 1624 is disposed towards the other, opposite side of the base portion 1620, and a third finger 1626 is disposed intermediate the first and second fingers 1622, 1624, although other configurations, including greater or fewer fingers, are also contemplated. As the fingers 1622, 1624, 1626 are spaced-apart relative to one another, first and second bays 1628, 1629 are defined between the fingers 1622, 1626 and the fingers 1624, 1626, respectively. Further, each of the fingers 1622, 1624, 1626 defines a lumen 1623, 1625, 1627 extending transversely therethrough. The lumens 1623, 1625, 1627 are aligned with one another in co-axial relation.

The cover flap 1640 includes a generally planar body portion 1642 and a pair of spaced-apart flanges 1646 extending from an end of the body portion 1642. Each of the flanges 1646 is formed integral with the body portion 1642 and includes a tubular end portion 1647 defining a lumen 1648 extending therethrough. The lumens 1648 are aligned in co-axial relation relative to one another.

In order to engage the cover flap 1640 with the base portion 1620, the cover flap 1640 is positioned such that the flanges 1646 thereof are disposed within the first and second bays 1628, 1629 and such that the lumens 1648 are aligned in co-axial relation with the lumens 1623, 1625, 1627. Thereafter, an engagement pin 1644 is inserted through the lumen 1623, one of the lumens 1648, the lumen 1627, the other of the lumens 1648, and the lumen 1625 (although the reverse order of insertion is also contemplated) to pivotably couple the base portion 1620 and cover flap 1640 to one another.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. For example, while the lid member is shown in the illustrated embodiments including a backing layer that is preferably paper, embodiments where the backing layer is not provided are also contemplated, as is forming the backing layer from alternate materials such as woven and non-woven fabrics. Therefore, the above description should not be construed as limiting, but merely as exemplifications of particular embodiments. Those skilled in the art will envision other modifications within the scope and spirit of the claims appended hereto.

What is claimed is:

1. A sample testing apparatus, comprising:
   a sample tray including first and second opposing sides defining a width therebetween and first and second opposing ends defining a length therebetween, the sample tray including a planar surface and a plurality of wells recessed relative to the planar surface, the plurality of wells including:
   a group of first wells arranged to define a matrix including a plurality of rows and a plurality of columns, the group of first wells disposed at the first end of the sample tray, each well of the group of first wells defining a first volume; and
   a group of second wells arranged to define a matrix including a single row and a plurality of columns, each well of the group of second wells defining an elongated configuration, oriented in a length-wise direction, defining a column of the plurality of columns, and extending from the group of first wells to the second end of the sample tray, each well of the group of second wells defining a second volume greater than the first volume; and
   a lid member initially sealed to the sample tray to define a pouch closed at the first end of the sample tray and open at or towards the second end of the sample tray, the lid member configured to be further sealed to at least a portion of the planar surface of the sample tray to enclose each well of the plurality of wells.

2. The sample testing apparatus according to claim 1, wherein the lid member is initially sealed to the sample tray about the first side, the first end, and the second side to define the pouch, and wherein the second end is open to permit introduction of a liquid sample into the pouch.

3. The sample testing apparatus according to claim 1, wherein the lid member is initially sealed to the sample tray entirely about the first side, the first end, the second side, and the second end to define the pouch therebetween, and wherein the sample tray defines a slit extending therethrough towards the second end thereof that is configured to permit introduction of a liquid sample into the pouch.

4. The sample testing apparatus according to claim 1, wherein the group of first wells defines a 9×10 matrix.

5. The sample testing apparatus according to claim 1, wherein the group of second wells includes six second wells.

6. The sample testing apparatus according to claim 1, wherein the lid member includes:
   an adhesive layer; and
   a breathable film layer disposed about the adhesive layer.

7. The sample testing apparatus according to claim 6, wherein the lid member further includes a removable backing layer disposed about the breathable film layer.

8. The apparatus according to claim 1, wherein the sample tray is formed from a blend of a styrene butadiene copolymer and general purpose polystyrene.

9. The sample testing apparatus according to claim 1, wherein an area of a base portion of each well of at least one of the groups of first or second wells is narrower than an area of an opening of each well of the at least one of the groups of first or second wells.

10. The sample testing apparatus according to claim 1, wherein each well of the group of second wells includes angled end walls.

11. The sample testing apparatus according to claim 10, wherein each well of the group of first wells defines a rectangular configuration with substantially vertical walls.

12. The sample testing apparatus according to claim 1, wherein the volume of each well of the group of second wells is plural times greater than the volume of each well of the group of first wells.

13. A sample testing apparatus, comprising:
   a sample tray including first and second opposing sides defining a width therebetween and first and second opposing ends defining a length therebetween, the sample tray including a plurality of wells including a group of first wells positioned at the first end of the sample tray and arranged to define a matrix having a plurality of rows and a plurality of columns, and a group of second wells arranged to define a matrix including a single row and a plurality of columns, each well of the group of second wells defining an elongated configuration, oriented in a length-wise direction, defining a column of the plurality of columns, and extending from the group of first wells to the second end of the sample tray, wherein each well of the group of first wells defines a first volume and wherein each well of the group of second wells defines a second volume different from the first volume; and
   a lid member sealed to the sample tray along the first end and the first and second sides of the sample tray to define a pouch, wherein the pouch closed at the first end of the sample tray and wherein an opening is defined at or towards the second end of the sample tray to permit introduction of a liquid sample into the pouch.

14. The sample testing apparatus according to claim 13, wherein the lid member is configured to be sealed to the sample tray along the second end of the sample tray after introduction of the liquid sample into the pouch.

15. The sample testing apparatus according to claim 13, wherein the sample tray defines a planar surface and wherein the plurality of wells are recessed from the planar surface.

16. The sample testing apparatus according to claim 15, wherein the sample tray is configured to flex from an at-rest position, wherein the planar surface is substantially planar, to a flexed position, wherein the planar surface is curved and the opening is enlarged to facilitate introducing the liquid sample into the pouch.

17. The sample testing apparatus according to claim 13, wherein the sample tray is configured such that introduction of the liquid sample through the opening to the closed end of the pouch fills the wells of the group of first wells completely before filling any of the wells of the group of second wells.

18. The sample testing apparatus according to claim 13, wherein the lid member includes a plurality of layers, the plurality of layers including:
   an adhesive layer configured to align with a top surface of the tray; and
   a permeable membrane layer disposed on the adhesive layer.

19. The sample testing apparatus according to claim 18, wherein the lid member further includes a removable backing layer disposed on the permeable membrane layer such that the permeable membrane layer is disposed between the removable backing layer and the adhesive layer.

20. The sample testing apparatus according to claim 13, wherein the second volume is greater than the first volume.

\* \* \* \* \*